United States Patent
Mori et al.

(10) Patent No.: US 7,430,282 B2
(45) Date of Patent: Sep. 30, 2008

(54) HEEL EFFECT COMPENSATION FILTER X-RAY IRRADIATOR, X-RAY CT SCANNER AND METHOD FOR X-RAY CT IMAGING

(75) Inventors: Shinichirou Mori, Chiba (JP); Masahiro Endo, Chiba (JP)

(73) Assignee: National Institute of Radiological Sciences, Chiba-shi, Chiba (JP)

( * ) Notice: Subject to any disclaimer, the term of this patent is extended or adjusted under 35 U.S.C. 154(b) by 182 days.

(21) Appl. No.: 10/594,513

(22) PCT Filed: Mar. 29, 2005

(86) PCT No.: PCT/JP2005/005972

§ 371 (c)(1),
(2), (4) Date: Sep. 28, 2006

(87) PCT Pub. No.: WO2005/092195

PCT Pub. Date: Oct. 6, 2005

(65) Prior Publication Data

US 2008/0123816 A1  May 29, 2008

(30) Foreign Application Priority Data

Mar. 29, 2004  (JP) ............................. 2004-095887

(51) Int. Cl.
*G21K 3/00* (2006.01)
(52) U.S. Cl. .................. 378/159; 378/145; 378/156
(58) Field of Classification Search ............... 378/156, 378/158, 159, 145
See application file for complete search history.

(56) References Cited

U.S. PATENT DOCUMENTS

| 6,327,329 | B1 | 12/2001 | Bromberg et al. |
| 6,968,042 | B2 * | 11/2005 | Toth et al. .................... 378/156 |
| 2005/0058254 | A1 * | 3/2005 | Toth et al. .................... 378/156 |
| 2005/0123100 | A1 * | 6/2005 | Hsieh .......................... 378/156 |
| 2006/0062353 | A1 * | 3/2006 | Yatsenko et al. ............ 378/156 |
| 2006/0256925 | A1 * | 11/2006 | Virshup et al. .............. 378/158 |

FOREIGN PATENT DOCUMENTS

| JP | 2000-790114 | 3/2000 |
| JP | 2004-214130 | 7/2004 |

OTHER PUBLICATIONS

"Mechanical Engineering of X-ray CT Scanner (5)-Artifact-, 6, Artifact Due to Cone-Angle of Multi-Slice CT", Jun. 2002, pp. 733-739.

* cited by examiner

*Primary Examiner*—Hoon Song
(74) *Attorney, Agent, or Firm*—Squire, Sanders & Dempsey L.L.P.

(57) ABSTRACT

A heel effect compensation filter is configured to have a thickness distribution that uniforms an X-ray intensity angular distribution that is nonuniform in the body axis direction of a subject in an X-ray flux irradiated space. The space is formed by an X-ray flux diverging from an anode in a body width direction of the subject and diverging in a shape of an approximate sector in the body axis direction due to the heel effect, when the X-ray flux generated on the anode by irradiating a thermoelectron beam flux from a cathode to the anode is irradiated on the subject. The thickness distribution can be obtained using a predetermined formula.

8 Claims, 14 Drawing Sheets

- 14 HEEL EFFECT COMPENSATION FILTER
- 14c CREST PART
- 14a CURVED SURFACE
- 14b FLAT SURFACE
- BODY WIDTH DIRECTION
- BODY AXIS DIRECTION

- BODY WIDTH DIRECTION
- 13b FLAT SURFACE
- 13 WEDGE FILTER
- BODY AXIS DIRECTION
- 13a CURVED SURFACE

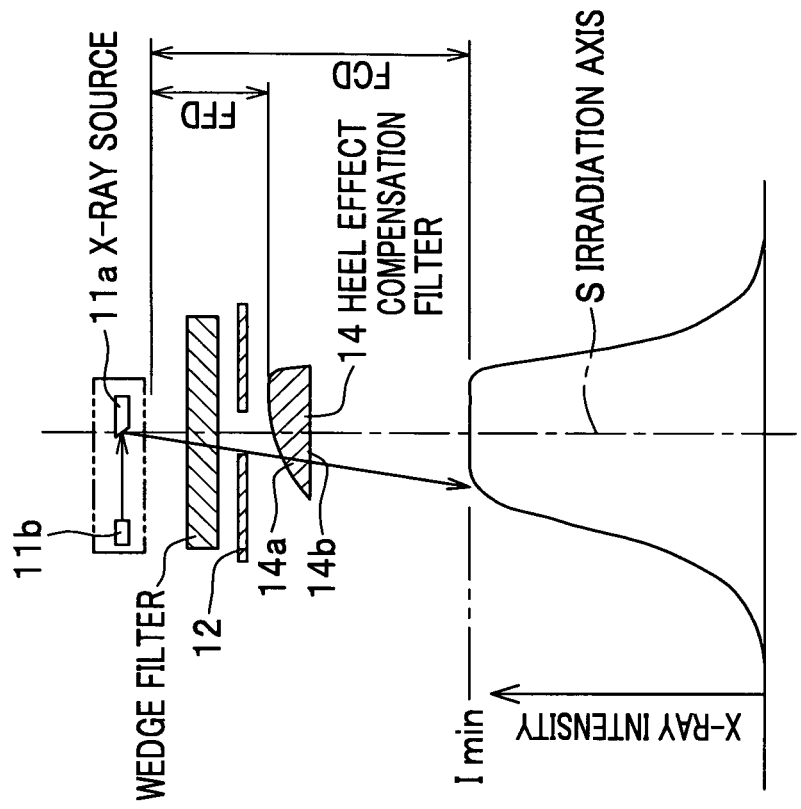
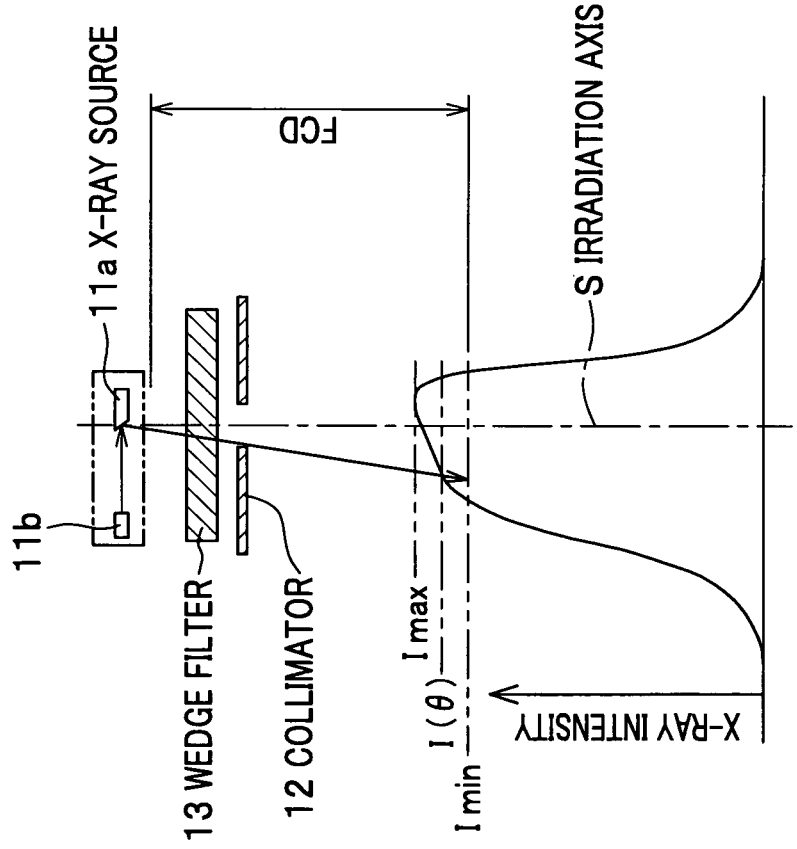

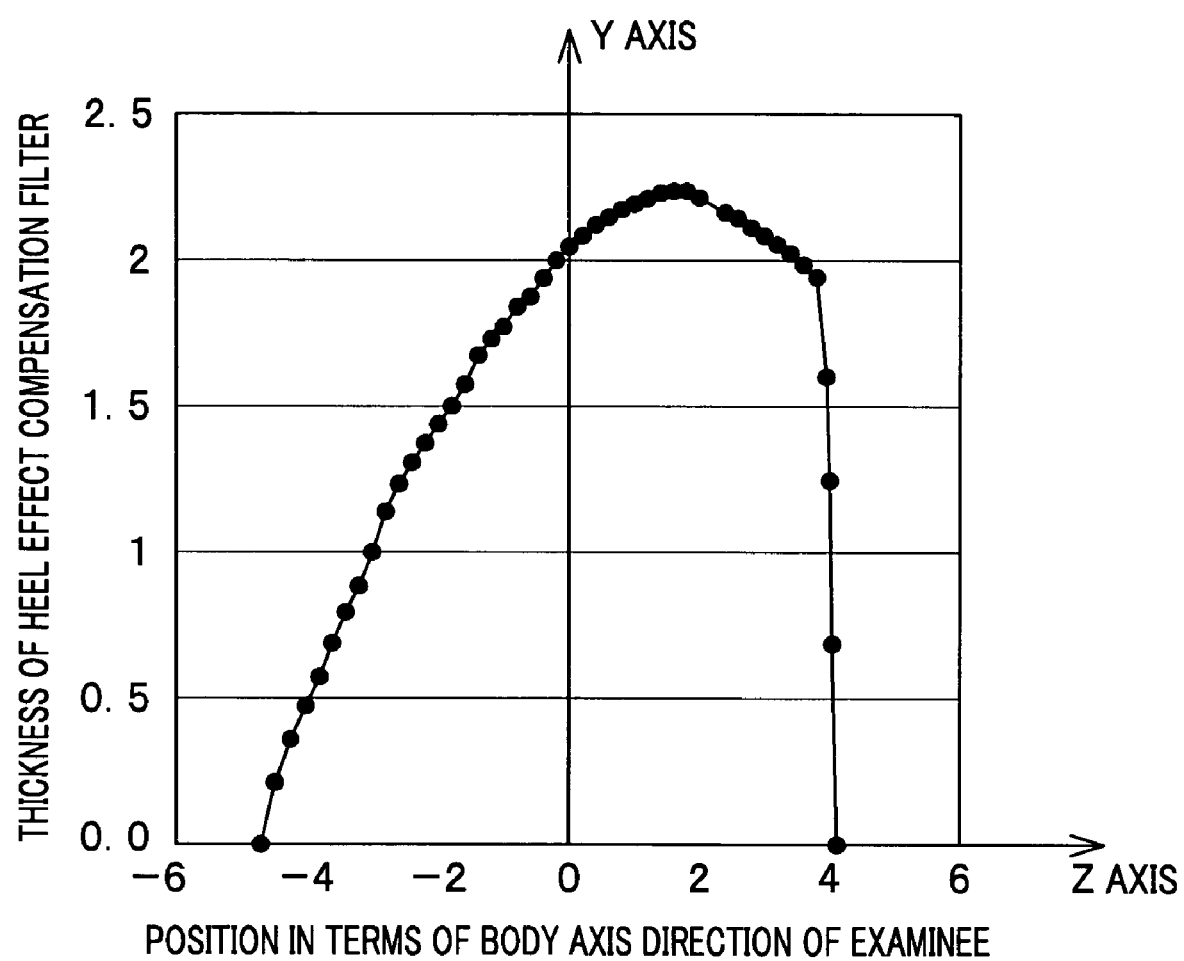

Conventional wedge

HEC wedge

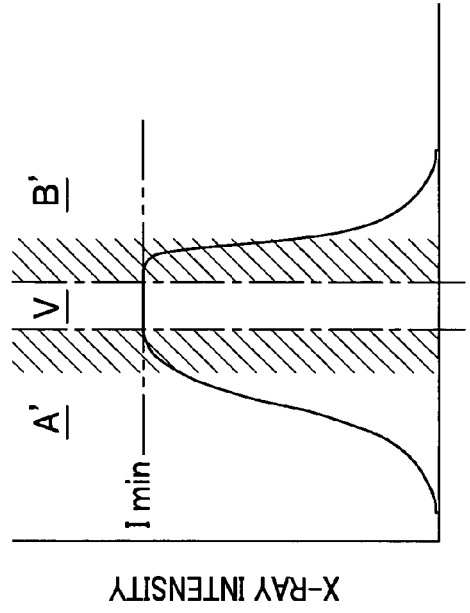
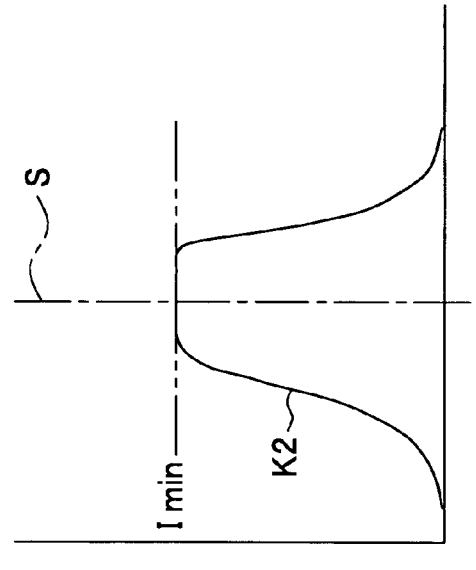
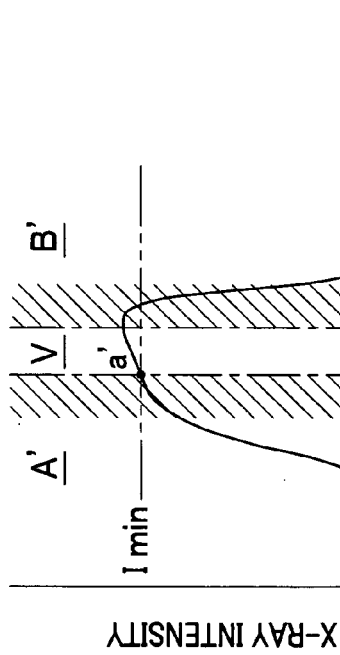
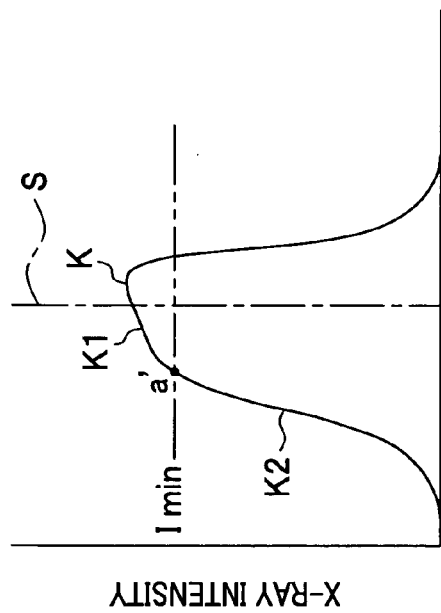

HEEL EFFECT COMPENSATION FILTER X-RAY IRRADIATOR, X-RAY CT SCANNER AND METHOD FOR X-RAY CT IMAGING

FIELD OF THE INVENTION

The present invention relates to a heel effect compensation filter, an X-ray irradiator and an X-ray CT scanner, which adjust a nonuniform X-ray intensity angular distribution of an X-ray flux due to a heel effect to become uniform when the X-ray flux is irradiated on a subject. The present invention also relates to a heel effect compensation filter, an X-ray irradiator, an X-ray CT scanner and an X-ray CT imaging method, with which image quality of image data obtained with the X-ray CT scanner is made uniform and improved in a body axis direction.

BACKGROUND ART

An X-ray generator in general is a device which irradiates a thermoelectron beam flux from a cathode to an anode, and generates an X-ray flux at the anode. The X-ray flux generated by the X-ray generator is irradiated on a subject, and the X-ray flux transmitted through the subject is detected by a predetermined detection means, to thereby obtain information of a part through which the X-ray flux has transmitted, as a slice image. A tomograph is a device which irradiates an X-ray flux from an X-ray generator on a subject, detects the X-ray flux transmitted through the subject by detection means arranged in a plane, and obtains slice data based on the detected information, which data is used for diagnosing a state of the slice.

As one of the most typical devices using an X-ray irradiator, an X-ray CT scanner (hereinbelow, referred to as "CT (Computed Tomography)") has been known. The CT is, for example, composed of an X-ray irradiator and a detection means which is a combination of a scintillator and a semiconductor device. However, for the CT, any device can be used in combination with the X-ray irradiator, as long as the device can detect an X-ray. The X-ray CT scanner is an X-ray diagnostic apparatus in which a large number of detectors each composed of a combination of the scintillator and the semiconductor device revolve around a body axis of a subject, while the X-ray irradiator and the detectors keep a flanking position relative to the subject, and slice images in a body width direction are continuously obtained in a body axis direction.

It should be noted that the body axis direction and the body width direction are orthogonal to each other, and an irradiation axis of the X-ray flux is orthogonal to both the body axis direction and the body width direction.

The CT is provided with a gantry and a platform. The gantry is formed in a shape of a thin-walled cylinder, and a central axis in a hollow part of the gantry is oriented so as to be included in a plane (hereinbelow, referred to as "axial plane") containing an incoming axis of the thermoelectron ray and an irradiation axis of the X-ray flux. The platform is placed to be movable backward and forward in the hollow part of the gantry in such a manner that the body axis of the subject to be subjected to the X-ray flux irradiation coincides with the central axis of the gantry. Further, the gantry has an X-ray tube and detectors at an opposed position to a position of the X-ray tube across the hollow part. As the X-ray tube and the detectors revolve around the body axis of the subject lying on the platform in the hollow part, the platform moves forward/backward. During this movement, the X-ray flux irradiated from the X-ray tube and transmitted through the subject is detected by the detectors to thereby obtain slice data along a predetermined length of the subject in the body axis direction. The slice data are subjected to computer analysis and a number of slice image data are created, which are then used for diagnosis of an inside of the subject.

Accordingly, based on differences in intensity of the incoming X-ray flux that has transmitted through the subject into respective detectors, a state of a slice part through which the X-ray has transmitted can be determined. In order to reduce exposure of the subject, it is preferred that an X-ray intensity angular distribution of the X-ray flux be made to fall in the lowest range that can be detected by the detectors, and at the same time, difference range of the X-ray flux intensity be made as small as possible.

The term "slice data" used herein means electrically generated data of a state of a slice part of the subject, based on the differences in intensity of the incoming X-ray flux that has transmitted through the subject into respective detectors.

The term "image data" used herein means data visually represented as an image based on the slice data.

In order to reduce the exposure of the subject as much as possible, the CT has the following means. For example, in a case where the subject is a human being (hereinbelow, frequently referred to as "examinee"), when the examinee at the irradiation position is seen in the body axis direction, a center of the examinee is the thickest and both ends in the body width direction are the thinnest. Therefore, during the X-ray flux irradiation, an absorption amount of the X-ray by the examinee body becomes largest at the central part of the body, and becomes smaller towards the both ends of the body. Attempts have been made to adjust such a difference in absorption of an X-ray flux in the body width direction due to the thickness of the examinee to fall in the lowest range that can be detected by the detectors (hereinbelow, referred to as "appropriate range"), by disposing a wedge filter between the X-ray tube and the examinee. The wedge filter is made of aluminum or the like, and a transmissive surface thereof is a cylindrical concave surface formed in such a manner that a vertical section seen in the body axis direction is in a shape of a concave lens which is axisymmetrical relative to the irradiation axis. With this configuration, a relatively strong X-ray that has transmitted through a central thinner part of the cylindrical concave wedge filter reaches the central part of the body, while a relatively weak X-ray that has transmitted through thicker lateral parts of the cylindrical concave wedge filter reaches thinner parts of the body. In this manner, the intensity of the X-ray flux is adjusted by the difference in the filter thickness so as to correspond the difference in body thickness while the X-ray flux transmits through the wedge filter.

It should be noted that, since the wedge filter revolves uniformly with the x-ray detector and the detectors, the filter in practice is designed based on a cross section of the examinee as a perfect circle.

On the other hand, in a case of X-ray flux irradiation in the body axis direction of the examinee, when the X-ray flux is irradiated by the X-ray generator, a phenomenon called "heel effect" occurs, in which an X-ray intensity angular distribution on an axis orthogonal to the irradiation axis at a predetermined distance from the anode becomes a shape with a cone angle (a shape of an approximate sector), on the axial plane containing the beam irradiation axis of the thermoelectron beam flux and the irradiation axis of the X-ray flux. Due to this heel effect, when the X-ray flux is irradiated on the examinee, the X-ray intensity angular distribution in the body axis direction becomes nonuniform. In other words, when obtaining slice data along the body axis, the thickness of the examinee body is considered to be even in the body axis direction, and an irradiation amount in this direction is kept uniform. As a result, at a portion with a strong X-ray irradiation intensity, the irradiation amount becomes excessively high, and the body part of the examinee is overexposed.

However, the overexposure due to this heel effect has not been taken into account, and a part of the slice data obtained by detecting the transmitted X-ray flux by the detector becomes blurry. For obtaining clear slice data, the heel effect has been cancelled merely by adjusting the obtained slice data themselves. For example, a proposal has been made in which an intensity distribution of various parts in the irradiation space of the X-ray flux is measured in advance by a sensor and the like without the examinee on the platform; data prepared in advance are referred to every time X-ray image is obtained; and the intensity distribution is adjusted by a computer program so that variation in the intensity distribution is cancelled (see, for example, Patent Document 1).

Recently, there has been disclosed an X-ray irradiator which uniformly irradiates X-ray by use of a metallic filter (see, for example, Patent Document 2).

Specifically, the invention disclosed in Patent Document 2 provides an X-ray irradiator having: an X-ray tube which outputs X-ray generated by irradiation of an electron beam on a target from an X-ray irradiation opening to outside; and a metallic filter which is attached to the X-ray irradiation opening of the X-ray tube and configured in such a manner that a portion of the filter exposed to a larger irradiation dosage is made thicker, based on the measurement of an X-ray dose distribution output from the X-ray irradiation opening of the X-ray tube.

In addition, there is a problem of artifacts (obstructive shadow) which are always present in X-ray CT imaging. An artifact is a phenomenon in which a virtual image is included in slice image data due to various factors, such as a failure of a device, defects in an image reconstruction system and scanning conditions. For example, it is considered that a ring-shaped artifact results from a failure of a detector, and that a beam hardening artifact results from a difference in energy of an outgoing X-ray due to energy absorption during transmission of an X-ray flux through a subject. Generation of artifacts lowers accuracy of diagnosis or the like on a subject based on slice image data.

In order to reduce generation of the artifacts, attempts has been made in which an image is first obtained and a cause is specified from a type and shape of the artifact and then removed; or in which image data are adjusted by a computer program (see, for example, Non-patent Document 1).

(Patent Document 1)

Japanese Unexamined Patent Publication Kokai No. 2000-079114 (paragraphs 0008-0029 and FIG. 2)

(Patent Document 2)

Japanese Unexamined Patent Publication Kokai No. 2004-214130 (claim 1)

(Non-Patent Document 1)

Katsumi Tsujioka, "Mechanical Engineering of X-ray CT scanner (5)-Artifact-" (PDF file), p 737, 6. Artifact Due to Cone-Angle of Multi-Slice CT, (online), Fujita Health University School of Health Sciences, (searched on Mar. 16, 2005), internet (URL: http://www.fujita-hu.ac.jp/~tsujioka/education.html)

DISCLOSURE OF THE INVENTION

Problem to be Solved by the Invention

Under the current situation as mentioned above with respect to the X-ray flux irradiation, a predominant type of the detector of the most recent CT has 16 arrays (arranged in the hollow part of the gantry in the axis direction). With a progress of accuracy and the like in adjustment of an X-ray image by a computer program, and an introduction of a larger number of arrays, such as 32 or more (e.g. 32, 40, 64, 124) arrays, various advantages are expected, such as speed-up of measurement time, high accuracy of an image, and three-dimensional imaging. At the same time, an irradiation width in the body axis direction of the subject is becoming larger. Consequently, unnecessary exposure due to the heel effect is anticipated to increase, with respect to a subject (for example, a patient at hospital) irradiated with an X-ray flux using an X-ray generator, such as a tomograph. A large amount of the X-ray flux irradiation will render the subject a heavy load, and if the X-ray flux is repeatedly irradiated, undesired disorder (including cancer development and other diseases) may be initiated in the examinee.

Under the current situation as mentioned above with respect to the X-ray CT scanner, there are problems in that CT imaging and data processing are time consuming and labor-some, for identifying and removing a cause of the artifact generation, and for adjusting image data by a computer program. Especially, in a case of the X-ray CT scanner having 32 arrays or more of detectors, the problem of the artifact becomes notable as in Non-Patent Document 1. Therefore, in development of the X-ray CT scanner having 32 arrays or more of detectors, it would be desirable to provide a method which reduces generation of artifacts when obtaining an X-ray CT image, not only when the image is processed after the X-ray CT imaging.

The present invention is made with the view toward solving the above-mentioned problems, and it is an object of the present invention to provide a heel effect compensation filter, an X-ray irradiator and an X-ray CT scanner, which uniform the X-ray intensity angular distribution of the X-ray flux that is nonuniform due to the heel effect, to thereby prevent the subject from being unnecessarily exposed to the X-ray. It is another object to provide a heel effect compensation filter, an X-ray irradiator, an X-ray CT scanner and an X-ray CT imaging method, with which an image quality of image data obtained with an X-ray CT scanner, especially an X-ray CT scanner having 32 arrays or more of detectors, is made uniform and improved in the body axis direction.

SUMMARY OF THE INVENTION

In order to solve the above-mentioned problems, a heel effect compensation filter according to the present invention as set forth in claim 1 is configured to have a thickness distribution that uniforms an X-ray intensity angular distribution that is nonuniform in a body axis direction of a subject in an X-ray flux irradiated space, the space being formed by an X-ray flux diverging from an anode in a body width direction of the subject and diverging in a shape of an approximate sector in the body axis direction orthogonal to the body width direction due to the X-ray intensity angular distribution affected by the heel effect, when the X-ray flux generated on the anode by irradiating a thermoelectron beam flux from a cathode to the anode is irradiated on the subject through a wedge filter configured to have a cylindrical concave surface with a curve being formed in the body width direction of the subject, wherein the thickness distribution is defined by Formula 1:

$$\begin{pmatrix} y' \\ z' \end{pmatrix} = \begin{pmatrix} L(\theta)\cos\theta \\ \dfrac{FFD}{FCD}(FCD\tan\theta - L(\theta)\sin\theta) \end{pmatrix} \quad \text{(Formula 1)}$$

($\theta \le |\text{cone angle}|$)

where, on a plane containing an irradiation axis of the X-ray flux and a beam irradiation axis of the thermoelectron beam flux, the irradiation axis of the X-ray flux is defined as a Y-axis, and an axis orthogonal to the Y-axis at a distance FCD along the Y-axis in a direction of X-ray flux irradiation is defined as a Z-axis; z' and y' represent positions in corresponding axial directions with the proviso that an intersection point of the Z-axis and the Y-axis is defined as an origin point; FFD is defined as a predetermined distance along the Y-axis from a position of the anode; θ is defined as a predetermined angle within a range of a cone angle symmetrically diverging from the position of the anode relative to the irradiation axis of X-ray flux; and La (θ) is defined as a length in a y' direction at the angle θ.

In accordance with the thickness distribution of the heel effect compensation filter obtained by the formula 1, the heel effect is adjusted so that the X-ray intensity angular distribution of the X-ray flux becomes uniform.

In addition, by obtaining the thickness distribution not based on a measured value of the X-ray angular distribution but by the formula, the filter can be easily designed.

Further, by obtaining the thickness distribution of the heel effect compensation filter by Formula 1, effective energy on an axis orthogonal to the irradiation axis at a predetermined distance from the anode can be made high and uniform on an axial plane containing the beam irradiation axis of the thermoelectron beam flux and the irradiation axis of the X-ray flux. When the effective energy of the incoming X-ray into the subject is high, energy absorption becomes poor during the transmission through the subject, and thus a difference in the effective energy of the outgoing X-ray from the subject becomes small. When such a heel effect compensation filter is employed in an X-ray CT scanner and the like, the generation of artifacts, such as a beam hardening artifact, is reduced, and image quality of image data is made uniform and improved in the body axis direction.

The heel effect compensation filter according to the present invention as set forth in claim 2 is the heel effect compensation filter of claim 1, wherein the heel effect compensation filter is separable into pieces and a distance in the heel effect compensation filter through which the X-ray flux transmits during usage is equal to the thickness distribution.

By defining the thickness distribution of the heel effect compensation filter based on the distance through which the X-ray flux transmits, the filter can be made in various shapes while retaining the above-mentioned predetermined effects.

The heel effect compensation filter according to the present invention as set forth in claim 3 is the heel effect compensation filter of claim 1 or 2, wherein either of an X-ray flux-incoming side transmissive surface and an X-ray flux-outgoing side transmissive surface may be configured as a cylindrical convex surface with a curve being formed in the body axis direction of the subject and the other may be configured as a flat surface.

By forming either of the X-ray flux-incoming side transmissive surface and the X-ray flux-outgoing side transmissive surface of the heel effect compensation filter as a curved surface and the other surface as a flat surface, the heel effect compensation filter can be easily designed, and processing cost can be suppressed.

The heel effect compensation filter according to the present invention as set forth in claim 4 is the heel effect compensation filter of claim 1 or 2, wherein either of an X-ray flux-incoming side transmissive surface and an X-ray flux-outgoing side transmissive surface may be configured as a cylindrical convex surface with a curve being formed in the body axis direction and the other may be configured as a cylindrical concave surface with a curve being formed in the body width direction orthogonal to the body axis direction.

Since single heel effect compensation filter has functions of a heel effect compensation filter and a wedge filter, an X-ray irradiator having the heel effect compensation filter can be made compact.

The heel effect compensation filter according to the present invention as set forth in claim 5 is the heel effect compensation filter of any one of claims 1-4, which may be employed in an X-ray CT scanner having 32 arrays or more of X-ray detectors.

By employing such a heel effect compensation filter in an X-ray CT scanner having 32 arrays or more of detectors, an X-ray intensity angular distribution of the X-ray flux becomes uniform, and therefore, unnecessary X-ray flux irradiation on the subject can be prevented. By using such an X-ray irradiator, artifacts, such as a beam hardening artifact, can be reduced, and image quality of image data can be made uniform in the body axis direction.

For example, especially in a case of the X-ray CT scanner having 32 arrays of detectors, artifacts are easily generated since effective energy of the X-ray flux is likely to become nonuniform. However, by using such a heel effect compensation filter, generation of the artifacts can be effectively reduced.

An X-ray irradiator according to the present invention as set forth in claim 6, in which a thermoelectron beam flux is irradiated from a cathode to an anode and an X-ray flux generated on the anode is irradiated on a subject, is characterized in that the heel effect compensation filter of any one of claims 1-5 is disposed between the anode and the subject at a predetermined distance, the filter being configured to adjust the X-ray intensity angular distribution of the X-ray flux to become uniform that is nonuniform in a body axis direction of the subject in an X-ray flux irradiated space, the space being formed by the X-ray flux diverging from the anode in a body width direction of the subject and diverging in a shape of an approximate sector in the body axis direction orthogonal to the body width direction due to the heel effect.

In this manner, by disposing the heel effect compensation filter between the anode and the subject at a predetermined distance, the X-ray intensity angular distribution of the X-ray flux becomes uniform, and therefore, unnecessary X-ray irradiation on the subject can be prevented.

In addition, by disposing the heel effect compensation filter between the anode and the subject at a predetermined distance, effective energy on an axis orthogonal to the irradiation axis at a predetermined distance from the anode can be made high and uniform on an axial plane containing the beam irradiation axis of the thermoelectron beam flux and the irradiation axis of the X-ray flux.

An X-ray CT scanner according to the present invention as set forth in claim 7 is characterized in that the scanner has the X-ray irradiator of claim 6.

Since the X-ray CT scanner of the present invention has an X-ray irradiator having a heel effect compensation filter, the X-ray intensity angular distribution of the X-ray flux transmitted through the heel effect compensation filter becomes uniform on an axial plane and a plane parallel to the axial plane. Therefore, unnecessary X-ray irradiation on the subject can be prevented.

In addition, since the X-ray CT scanner of the present invention has an X-ray irradiator having a heel effect compensation filter, the effective energy of the X-ray flux transmitted through the heel effect compensation filter becomes high and uniform in a predetermined direction. At the same time the artifacts, especially a beam hardening artifact, can be reduced, and image quality of image data can be made uniform in the body axis direction.

A method for X-ray CT imaging according to the present invention as set forth in claim 8 is characterized in that, for reducing an artifact of image data obtained by an X-ray CT scanner, the method employs the heel effect compensation filter of any one of claims 1-5 in the X-ray CT scanner and reduces a difference in CT value of the image data obtained along a body axis direction.

Since, in the X-ray CT imaging method of the present invention, a heel effect compensation filter is employed in the X-ray CT scanner, the effective energy becomes high and uniform in a predetermined direction, after the X-ray flux that has been irradiated from the anode of the X-ray CT scanner transmitted through the heel effect compensation filter. At the same time the artifacts, especially a beam hardening artifact, can be reduced, and image quality of image data obtained with an X-ray CT scanner can be made uniform and improved in the body axis direction.

Effect of the Invention

According to the heel effect compensation filter, the X-ray intensity angular distribution of the X-ray flux which is nonuniform due to the heel effect can be made uniform. In addition, according to the heel effect compensation filter, the effective energy can be made high and uniform in a predetermined direction.

According to the X-ray irradiator, the X-ray intensity angular distribution of the X-ray flux which is nonuniform due to the heel effect can be made uniform, and therefore, unnecessary exposure of the subject can be reduced. In addition, according to the X-ray irradiator, the effective energy can be made high and uniform in a predetermined direction.

According to the X-ray CT scanner, the X-ray intensity angular distribution of the X-ray flux which is nonuniform due to the heel effect can be made uniform, and therefore, unnecessary exposure of the subject can be reduced. In addition, according to the X-ray CT scanner, the effective energy can be made high and uniform in a predetermined direction. At the same time, the artifacts, especially a beam hardening artifact, can be reduced, and image quality of image data can be made uniform in the body axis direction.

According to the X-ray CT imaging method, the effective energy can be made high and uniform in a predetermined direction, at the same time, the artifacts, especially a beam hardening artifact, can be reduced, and image quality of image data can be made uniform in the body axis direction.

BRIEF DESCRIPTION OF THE DRAWINGS

FIG. 6(a) is a diagram showing a maximum value and a minimum value of an X-ray intensity, and (b) is a diagram showing a condition where the X-ray intensity is uniform at a minimum value.

FIG. 7 is a graph showing a thickness distribution of a heel effect compensation filter.

FIG. 14 shows X-ray intensity maps in different X-ray irradiators. (a) is an X-ray intensity map in a case where an X-ray flux is irradiated through a collimator, (c) is an X-ray intensity angular map in a case where an X-ray flux is irradiated without regulation by, especially collimator or the like. (b) and (d) show cases where appropriate heel effect compensation filters are used in (a) and (c), respectively.

DESCRIPTION FOR REFERENCE CHARACTERS

Figure 1:
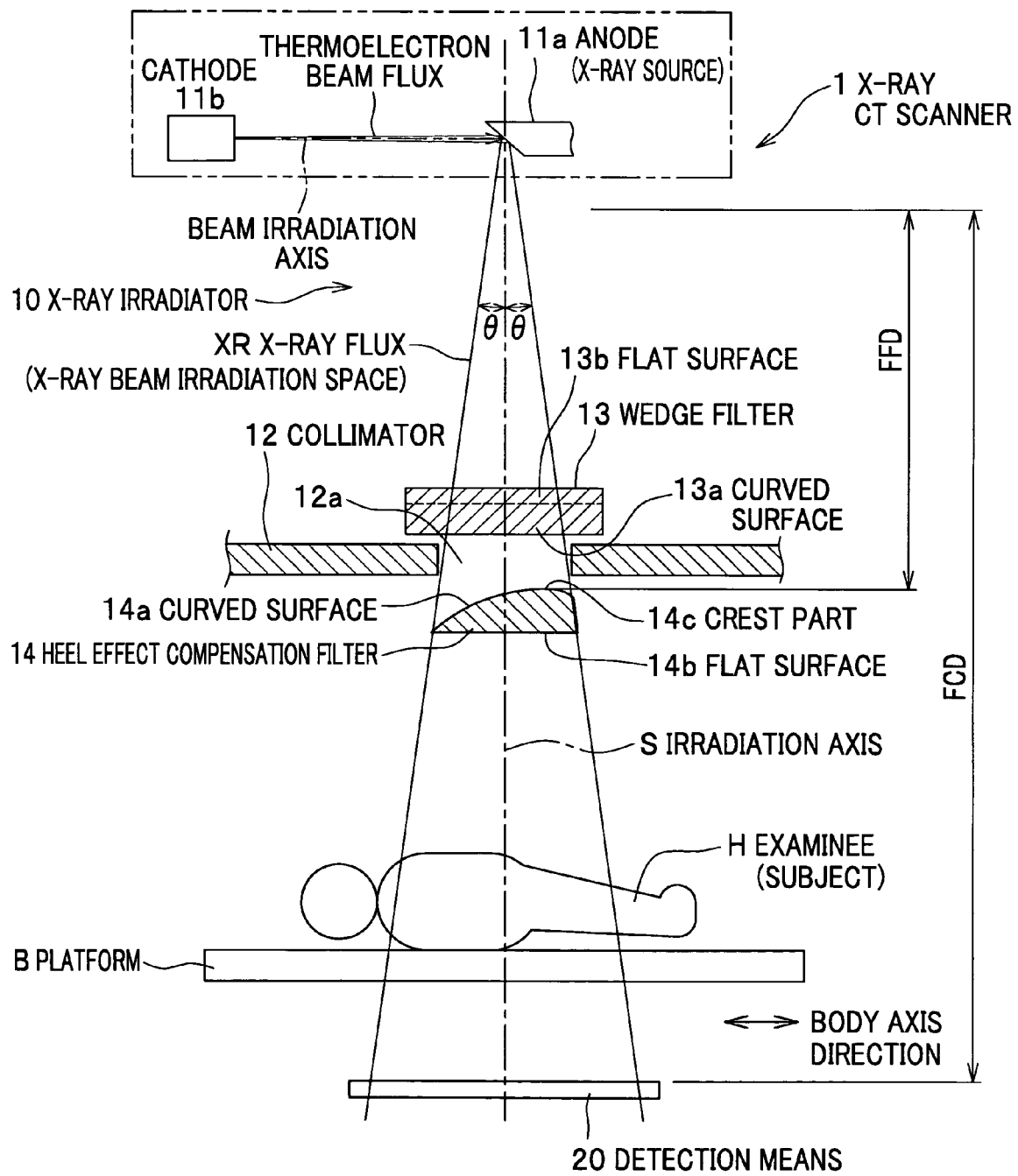
FIG. 1 is a plan view diagrammatically showing one example of an X-ray irradiator according to a first embodiment of the present invention.

1 X-ray CT scanner
10 X-ray irradiator
11a anode (X-ray source)
11b cathode
13 wedge filter
13a curved surface
14a, 15a curved surface
13b, 14b flat surface
14, 15 heel effect compensation filter
14c, 15c crest part
15b curved surface
20 detection means
XR X-ray flux
S irradiation axis
H examinee (subject)
B platform

DESCRIPTION OF THE PREFERRED EMBODIMENTS

The best mode for carrying out the present invention will be described in detail below with reference to the drawings.

In each embodiment, descriptions are made by assuming that the subject is a patient treated at a hospital (hereinbelow, also referred to as "examinee").

Also descriptions are made for a case where the heel effect compensation filter and the X-ray irradiator of the present invention are used in an X-ray CT scanner.

A direction of X-ray flux irradiation is defined as a direction orthogonal to a both body width direction and a body axis direction relative to an examinee H, which directions are also orthogonal to each other.

First Embodiment

Figure 2:
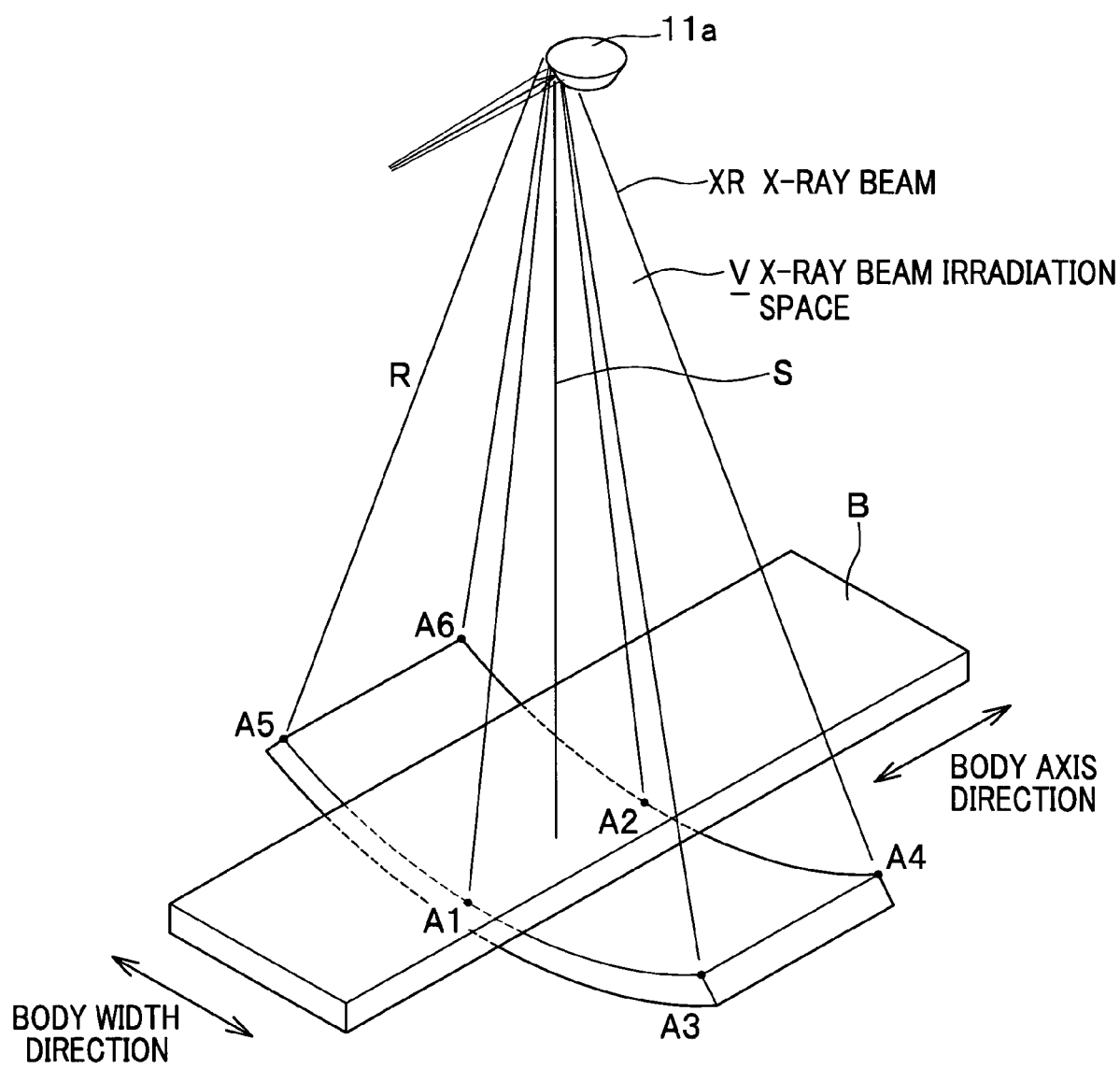
FIG. 2 is a diagram showing one example of an X-ray flux irradiated space of the irradiated X-ray flux.
Figure 3A:
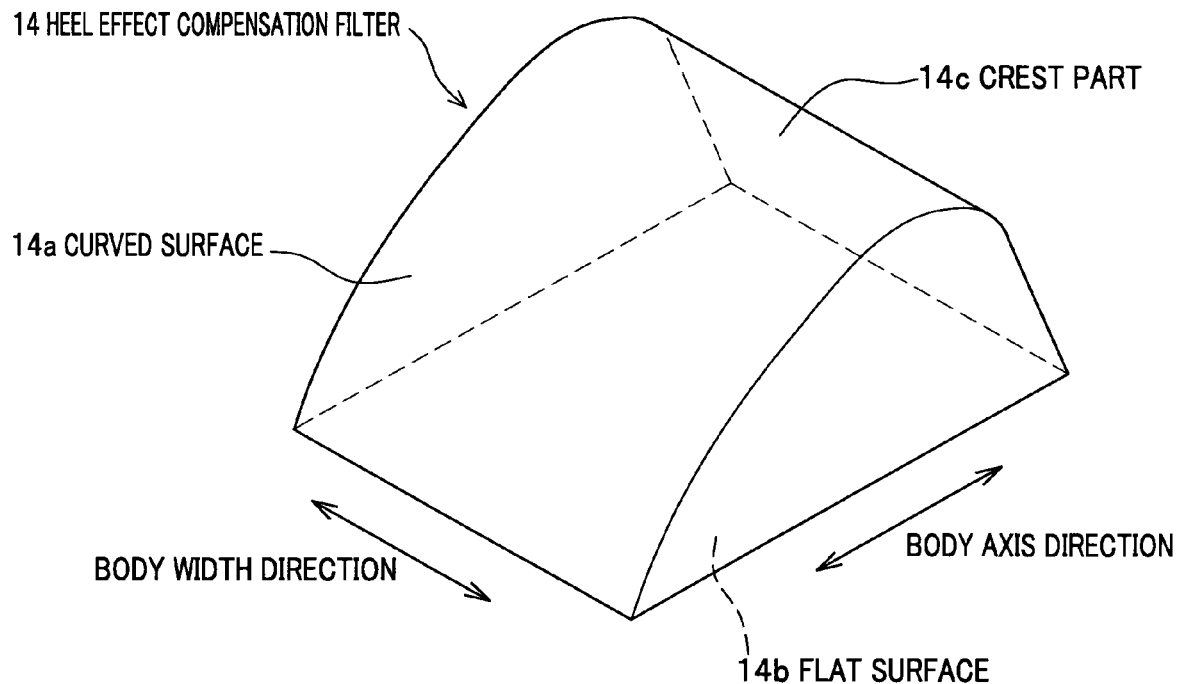
FIG. 3(a) is a perspective view showing one example of a heel effect compensation filter, and (b) is a perspective view showing one example of a wedge filter.
Figure 4A:
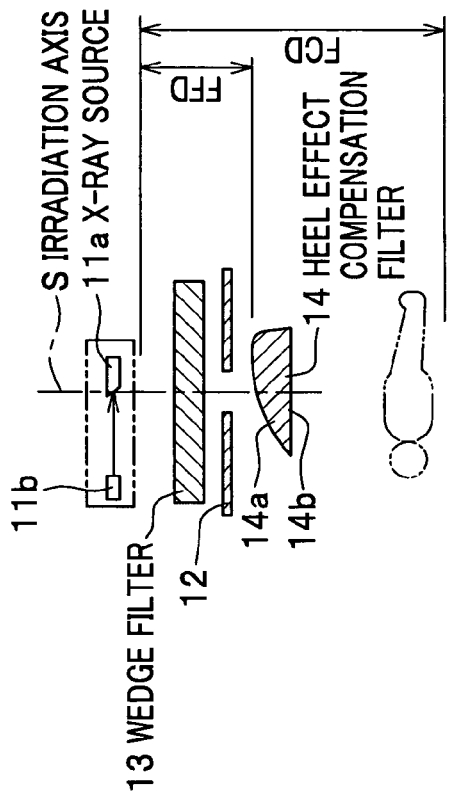
FIG. 4(a) is a diagram showing a case where a heel effect compensation filter is not used, (b) is an X-ray intensity map showing the case where the heel effect compensation filter is not used, (c) is a diagram showing a case where the heel effect compensation filter is used, and (d) is a graph of an X-ray intensity angular distribution showing the case where the heel effect compensation filter is used.
Figure 5:
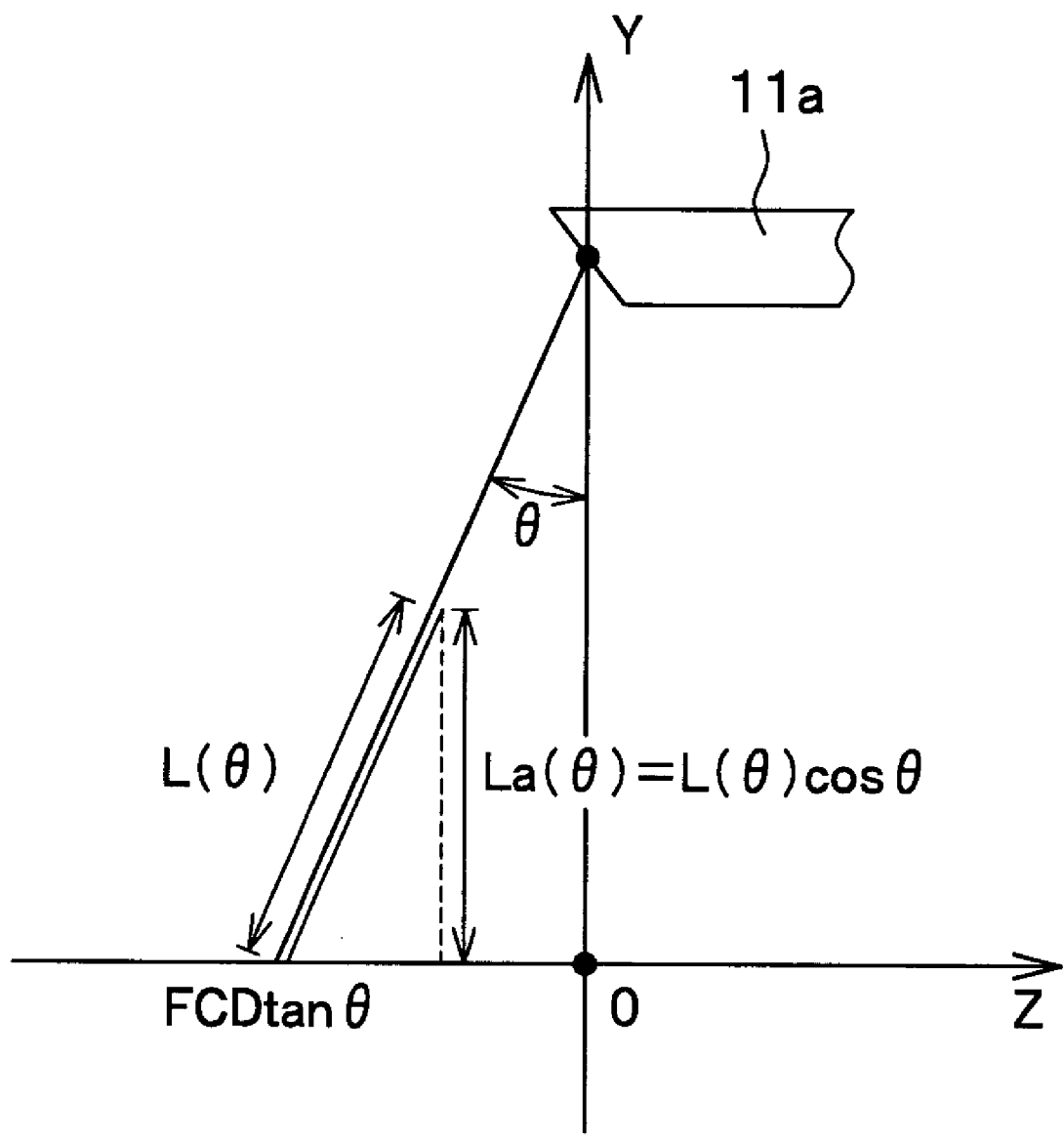
FIG. 5 is a diagram showing a positional relationship of signs to be used in a formula.

FIG. 1 is a plan view diagrammatically showing one example of X-ray irradiator according to a first embodiment of the present invention. FIG. 2 is a diagram showing one example of an X-ray flux irradiated space of the irradiated X-ray flux. FIG. 3(a) is a perspective view showing one example of a heel effect compensation filter, and (b) is a perspective view showing one example of a wedge filter. FIG. 4(a) is a diagram showing a case where a heel effect compensation filter is not used, (b) is an X-ray intensity map showing a case where the heel effect compensation filter is not used, (c) is a diagram showing a case where the heel effect compensation filter is used, and (d) is a graph of an X-ray intensity angular distribution showing a case where the heel effect compensation filter is used. FIG. 5 is a diagram showing a positional relationship of signs to be used in a formula. FIG. 6(a) is a diagram showing a maximum value and a minimum value of an X-ray intensity, and (b) is a diagram showing a condition where the X-ray intensity is uniform at a minimum value. FIG. 7 is a graph showing a thickness distribution of a heel effect compensation filter.

An X-ray CT scanner 1 according to a first embodiment of the present invention includes an X-ray irradiator 10, a detection means 20, a platform B and a gantry (not shown). The X-ray irradiator 10 irradiates an X-ray flux on an examinee H lying on the platform B as the X-ray irradiator 10 revolves around the body axis of the subject, while the platform B moves forward and backward. During this movement, the detection means 20 captures the X-ray flux that has transmitted through the examinee and produces slice data, which is then subjected to image processing by a computer (not shown) and converted into image data. The image data of a predetermined length in the body axis direction of the examinee H is displayed on a monitor or printed on a film, which is utilized in diagnosis on the examinee H.

The gantry is configured to have a cylindrical shape, and on an inner periphery thereof, the X-ray irradiator 10 and the detection means 20 composed of a number of detectors are placed in such a manner that the X-ray irradiator 10 and the detection means 20 are opposed to each other by sandwiching a hollow space of the gantry therebetween. The detectors are arranged on an arc having a center on the anode. In the hollow space of the gantry, the platform B is disposed to be movable forward and backward.

For example, the body axis direction of the examinee H is in parallel with a moving direction of the platform B, and the body width direction of the examinee H is in parallel with the width direction of the platform B.

For the detection means 20, any conventional detection means can be used. As mentioned above, the detection means 20 is configured to detect an X-ray flux XR transmitted through the examinee H lying on the platform B disposed between the X-ray irradiator 10 and the detection means 20, and to generate slice data from the X-ray flux XR after detecting the X-ray flux XR transmitted through the examinee H.

The detection means 20 is arranged, in the body width direction, on an arc having a radius R which has an origin point on the anode 11a so that a distance from the anode 11a to the detection means 20 becomes a predetermined constant distance R.

The X-ray irradiator 10 is disposed in the gantry (not shown), and as shown in FIG. 1, irradiates the X-ray flux XR from the anode (hereinbelow, referred to as "X-ray source") 11a in such a manner that the X-ray intensity angular distribution of the X-ray flux XR transmitted through the examinee H becomes uniform on a platform B-side surface of the detection means 20. The X-ray irradiator 10 includes a cathode 11b, the X-ray source 11a, a collimator 12, a wedge filter 13 having a cylindrical concave surface 13a, and a heel effect compensation filter 14 having a cylindrical convex surface 14a.

In this X-ray irradiator 10, the X-ray flux XR passes through the heel effect compensation filter 14 which will be described below, and therefore the X-ray intensity angular distribution of the X-ray flux XR in the body axis direction of the examinee H becomes uniform.

First, a mechanism of X-ray flux XR irradiation will be described.

A thermoelectron beam flux, irradiated from the cathode 11b and accelerated by an electric field, collides with a rotating X-ray source 11a in a form of a disk (not shown), and an impact of the collision generates an X-ray flux XR which is then irradiated in a constant direction forming a predetermined angle α (not shown) together with the thermoelectron beam. In general, the cathode 11b and the X-ray source 11a are sealed in an X-ray tube casing (not shown) with insulating oil, for the purpose of stabilizing an irradiation direction. In the cathode 11b, there is provided a linear filament (not shown) to release thermoelectrons by heating. On the other hand, although not shown, the rotating disk-shaped X-ray source 11a as a whole is made of tungsten, and has a face piece, called "target", against which the thermoelectrons collide, provided with an inclination in order to irradiate the X-ray flux XR in a constant direction. As a result of the impact by collision of the thermoelectrons against the inclined target surface, the X-ray flux XR is irradiated from the target in a constant direction. In contrast, an X-ray intensity angular distribution on an axial plane becomes a shape of an approximate sector. This is what is called "heel effect" described above.

Referring to FIG. 2, the X-ray flux XR diverges from the X-ray source 11a in the body width direction of the examinee H and, due to the heel effect, diverges in a shape of an approximate sector in the body axis direction of the examinee H orthogonal to the body width direction, to thereby form an X-ray flux irradiated space V.

The X-ray flux irradiated space V reaches the detection means 20, which is in a shape of an arc in the body width direction and has a center on the X-ray source 11a.

In this case, for example, along a line A1-A2 orthogonal to the body width direction and to an irradiation axis S of the X-ray flux XR, the X-ray intensity angular distribution of the X-ray flux XR becomes uniform.

Also along lines A3-A4 and A5-A6 on the detection means 20, the X-ray intensity angular distribution of the X-ray flux XR becomes uniform.

In this manner, the X-ray intensity angular distribution of the X-ray flux XR also becomes uniform, on the surface areas in the body axis direction of the detection means 20 which is in a shape of an arc in the body width direction.

It should be noted that, in the present embodiment, the term "array" used in description of configurations of an X-ray CT scanner is a general term to be used for describing configurations of X-ray CT scanners, and referring to FIG. 2, the term means a number of rows of the scintillators to be used in the detection means 20 for detecting irradiation, along the body axis direction, such as lines A1-A2, A3-A4 and A5-A6.

Next, positional relationships of components will be described.

As shown in FIG. 1, the irradiation axis S of the X-ray flux XR forms a predetermined angle together with the beam irradiation axis from the cathode 11b, and is set in a direction to transmit through the examinee H lying on the platform B.

The heel effect compensation filter 14 is disposed at a predetermined distance FFD from the X-ray source 11a so as to intersect the irradiation axis S of the X-ray flux XR. In addition, the collimator 12 is disposed between the X-ray source 11a and the heel effect compensation filter 14, and a wedge filter 13 is disposed between the X-ray source 11a and the collimator 12. Each component will be described in detail below.

The X-ray source 11a irradiates the examinee H with the X-ray flux XR. During irradiation, the X-ray flux XR is irradiated in such a manner that the irradiation space diverges from the X-ray source 11a as an origin point with an angle θ relative to the irradiation axis S, as the X-ray flux XR approaches the examinee H.

The collimator 12 is a plate member having an opening 12a at the center of the surface thereof. The collimator 12 is disposed between the X-ray source 11a and the examinee H, and only the X-ray flux XR that has passed the opening 12a is irradiated on the examinee H.

The heel effect compensation filter 14 is made of aluminum, and as shown in FIGS. 1 and 3(a), an X-ray flux XR-incoming side transmissive surface is formed as a cylindrical convex (approximately hog-backed) surface 14a extending in a direction orthogonal to an axial plane, and a transmissive surface on an examinee H side, i.e. an X-ray flux-outgoing side opposite to the cylindrical convex surface 14a is formed as a flat surface 14b. The heel effect compensation filter 14 has a function of adjusting an X-ray intensity angular distribution of the X-ray flux XR irradiated from the X-ray source 11a to become uniform in the body axis direction.

The cylindrical convex surface 14a of the heel effect compensation filter 14 is formed in such a manner that a distance relative to the flat surface 14b changes in the body axis direction. With this configuration, when the X-ray flux XR transmits through the heel effect compensation filter 14, the X-ray intensity angular distribution of the X-ray flux XR in the X-ray flux irradiated space V becomes continuously uniform in the body axis direction. Since the subject is considered to have the same thickness in the body axis direction, the X-ray intensity angular distribution becomes uniform in the body axis direction after the X-ray flux XR transmitted through the subject. In FIG. 1, the heel effect compensation filter 14 is disposed between the collimator 12 and the examinee H at a position proximate to the collimator 12. In addition, the heel effect compensation filter 14 is positioned so that a minimum distance between the X-ray source 11a and an axis which is orthogonal to the irradiation axis S and passes through the crest part 14c of a cylindrical convex surface 14a of the heel effect compensation filter 14 becomes a predetermined distance FFD. By positioning the heel effect compensation filter 14 in this manner, a predetermined distance FCD from the X-ray source 11a matches with the position of the detection means 20, and the X-ray intensity angular distribution of the X-ray flux XR becomes uniform along the detection means 20. It should be noted that a value of the predetermined distance FCD is larger than that of the predetermined distance FFD.

A thickness distribution of the heel effect compensation filter 14 is configured in such a manner that, as shown in FIG. 7, in the body axis direction of the examinee H, the thickness gradually increases from one end of the heel effect compensation filter 14, the thickness becomes maximum at a position away from the irradiation axis S of the X-ray flux XR to form the crest part 14c, and the thickness decreases towards the other end.

The reason for this thickness distribution of the heel effect compensation filter 14 is as follows. Suppose there is a predetermined vertical line, which is in parallel with the body axis direction of the examinee H and is orthogonal to an irradiation axis S of the X-ray flux XR (for example, an X-ray intensity Imin shown in FIG. 6(a)) and crosses the X-ray intensity angular distribution. Provided that the X-ray intensity angular distribution of the X-ray flux XR at an intersection of the vertical line with the X-ray intensity angular distribution is a standard (base), an intensity of the X-ray flux XR becomes maximum at a position away from the irradiation axis S, and the intensity of the X-ray flux XR gradually decreases from that position towards the intersection of the vertical line with the X-ray intensity angular distribution, since the X-ray intensity angular distribution of the X-ray flux XR diverges in a shape of an approximate sector due to the heel effect. In order to deal with this intensity, the filter is made thicker at the position where an X-ray intensity is stronger, while the filter is made thinner at the position where the X-ray intensity is weaker.

It should be noted that a minimum value of the X-ray intensity Imin, which is a criterion for calculating a thickness distribution of the heel effect compensation filter 14, can be selected depending on a configuration of the X-ray irradiator 10 used.

FIG. 14 shows X-ray intensity maps in different X-ray irradiators. (a) is an X-ray intensity angular map in a case where an X-ray flux is irradiated through a collimator which regulates a shape of an X-ray flux irradiated space, (c) is an X-ray intensity angular map in a case where an X-ray flux is irradiated without regulation of a shape of an X-ray flux irradiated space by, especially collimator or the like. (b) and (d) show intensity maps for an X-ray flux XR in cases where appropriate heel effect compensation filters 14 are used in (a) and (c), respectively.

In FIG. 14(a), of the X-ray flux irradiated space, an A' space on a cathode 11b side and a B' space on an anode 11a side are regulated by the collimator 12. In FIG. 14(a), a boundary point a' between the A' space and the X-ray irradiated space V indicates a minimum X-ray intensity (Imin) in the X-ray irradiated space V. Accordingly, the thickness distribution of the heel effect compensation filter 14 can be made such that the intensity distribution of the X-ray flux XR becomes uniform at Imin. In a case where such a heel effect compensation filter 14 is employed in the X-ray irradiator 10 shown in FIG. 14(a), an X-ray intensity distribution as shown in FIG. 14(b) is obtained.

In FIG. 14(c), the X-ray flux irradiated space V is not regulated specifically by the collimator 12 or the like. As shown in FIG. 14(c), the X-ray intensity angular distribution typically contains: a maximum point K at a predetermined distance from the irradiation axis S where the X-ray intensity becomes maximum; a first inclination K1 in which the X-ray intensity decreases from the maximum point K to the cathode 11b side; and a second inclination K2 which is continuous with the first inclination, in which the X-ray intensity decreases with a larger inclination than the first inclination. An X-ray intensity at a boundary point a' between the first inclination K1 and the second inclination K2 is set to Imin, and the thickness distribution of the heel effect compensation filter 14 can be made such that the intensity distribution of the X-ray flux XR becomes uniform at Imin. In a case where such a heel effect compensation filter is employed in the X-ray irradiator shown in FIG. 14(c), an X-ray intensity distribution as shown in FIG. 14(d) is obtained.

By using the minimum value of the X-ray intensity Imin obtained in such a manner, the thickness distribution of the heel effect compensation filter 14 can be obtained in the following manner.

Figure 4B:
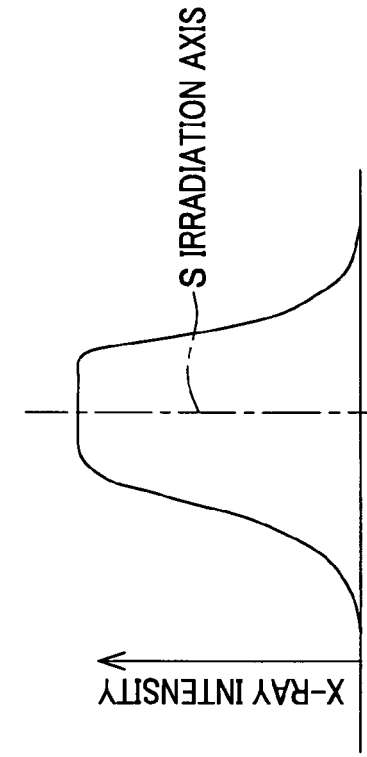

In the case where the heel effect compensation filter 14 is not used like FIG. 4(a), the intensity of the X-ray flux XR that has passed through the opening 12a of the collimator 12 becomes maximum at a position away from the irradiation axis S and gradually decreases at a position further away from that point as shown in FIG. 4(b). In order to convert a non-uniform X-ray intensity angular distribution into a uniform one, the cylindrical convex surface 14a is formed as described above.

Figure 4C:
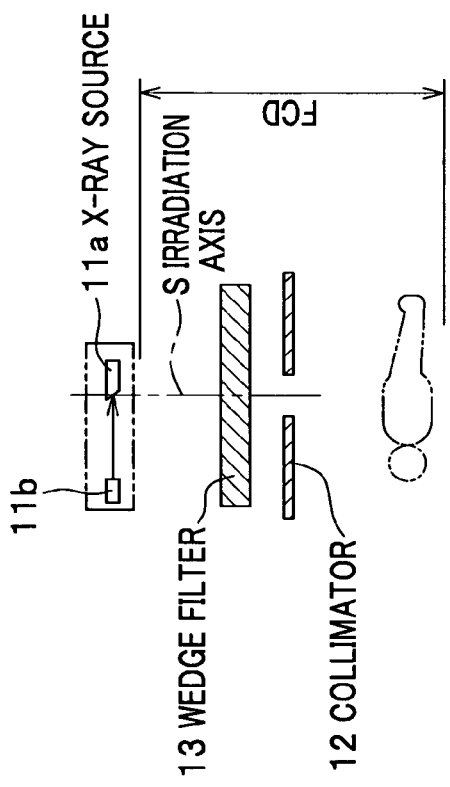
Figure 4D:
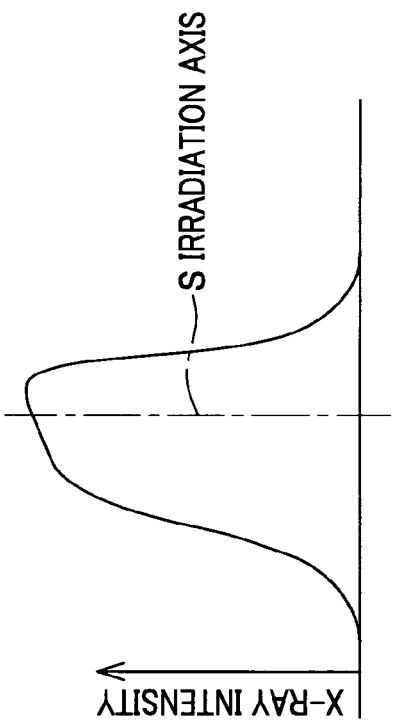

Therefore, as shown in FIG. 4(c), in the case where the heel effect compensation filter 14 is used, as shown in FIG. 4(d), at the position where the intensity of the incoming X-ray flux XR into the heel effect compensation filter 14 is maximum, the heel effect compensation filter 14 is made thickest while at the position where the intensity of the X-ray flux XR is weaker, the heel effect compensation filter 14 is made thinner. Therefore, the X-ray intensity angular distribution of the X-ray flux XR becomes uniform in the body axis direction of the examinee H, at a predetermined distance FCD from the X-ray source 11a.

It should be noted that the thickness distribution of the heel effect compensation filter 14 can be also obtained from the following Formula 1.

$$\begin{pmatrix} y' \\ z' \end{pmatrix} = \begin{pmatrix} L(\theta)\cos\theta \\ \frac{FFD}{FCD}(FCD\tan\theta - L(\theta)\sin\theta) \end{pmatrix} \quad \text{(Formula 1)}$$

($\theta \leq |\text{cone angle}|$)

In short, on a plane containing the irradiation axis S of the X-ray flux XR and the beam irradiation axis of the thermo-electron beam flux, as shown in FIG. 5, the irradiation axis S of the X-ray flux XR is defined as a Y-axis, and a position at a distance FCD away from the focal point on the Y-axis (i.e. X-ray source 11a) is defined as an origin point of the coordinate axes (Y-Z). An axis passing the origin point and being orthogonal to the Y-axis, and in parallel with the body axis direction of the examinee H is defined as a Z-axis. The distance FCD is a distance from the X-ray source 11a to the isocenter, i.e. a distance to the platform B side detection means 20.

In addition, with respect to a divergence angle $\theta$ of the X-ray flux XR relative to the irradiation axis S of the X-ray flux XR, an intensity of the X-ray flux XR before transmitting through the heel effect compensation filter 14 is defined as $I_0(\theta)$, while an intensity of the X-ray flux XR after transmitting through the heel effect compensation filter 14 is defined as $I(\theta)$. An apparent thickness of the heel effect compensation filter 14 for an angle $\theta$ is defined as $L(\theta)$. The $\theta$ is a predetermined angle within a range of cone angle formed by symmetrically diverging from the X-ray source 11a with the irradiation axis of the X-ray flux as an axis of symmetry. The letters "z" and "y" in the formula represent positions in respective axial directions with an intersection of the Z-axis and the Y-axis as an origin point, and "FFD" represents a predetermined distance from the X-ray source 11a along the Y-axis.

In this case, when the X-ray flux XR transmits through the heel effect compensation filter 14 at an angle $\theta$, the apparent thickness $L(\theta)$ is expressed as an inclined distance, which is then converted into a length in a Y-axis direction (thickness) $La(\theta)$.

Subsequently, within a range where the X-ray intensity angular distribution is adjusted as shown in FIG. 6(a), a fitting function which will be described below is assigned. Upon assigning, the maximum value and the minimum value of the X-ray intensity and the X-ray intensity at an angle $\theta$ are represented as Imax, Imin and $I(\theta)$, respectively. An attenuation coefficient is represented as $\mu$.

In addition, as shown in FIG. 6(b), in order to convert $I(\theta)$ to Imin, a required apparent thickness $L(\theta)$ is obtained by the following Formula 2:

$$I(\theta) = I_0(\theta) \text{EXP}(-\mu x) \quad \text{(Formula 2)}$$

where x is an apparent thickness.

By assigning $L(\theta)$ to x and Imin to $I_0(\theta)$ and rewriting the formula for $L(\theta)$, the formula above is expressed as the following Formula 3:

$$L(\theta) = 1/\mu \times \ln(I(\theta)/I\text{min}) \quad \text{(Formula 3)}$$

In order to obtain an actual thickness $La(\theta)$, the above formula is resolved into y and z components as shown in the following Formula 4:

$$\begin{pmatrix} y \\ z \end{pmatrix} = \begin{pmatrix} L(\theta)\cos\theta \\ FCD\tan\theta - L(\theta)\sin\theta \end{pmatrix} \quad \text{(Formula 4)}$$

Provided that the heel effect compensation filter 14 is installed at a distance FFD away from the focal point, Formula 4 can be expressed as Formula 1 shown below.

In the formula, y' and z' mean a thickness relative to a position in the body axis direction and a position in the body axis direction, respectively.

$$\begin{pmatrix} y' \\ z' \end{pmatrix} = \begin{pmatrix} L(\theta)\cos\theta \\ \frac{FFD}{FCD}(FCD\tan\theta - L(\theta)\sin\theta) \end{pmatrix} \quad \text{(Formula 1)}$$

($\theta \leq |\text{cone angle}|$)

By eliminating a trigonometric function from this formula, the following Formula 5 is obtained.

$$z' = \frac{FFD}{FCD}\left(\frac{FCD}{y'} - 1\right)\sqrt{L(\theta)^2 - y'^2} \quad \text{(Formula 5)}$$

By solving this Formula 5 for y', the thickness of the heel effect compensation filter 14 $La(\theta)$ can be obtained.

With respect to the heel effect compensation filter 14 formed according to this Formula 1, the cylindrical convex surface 14a may be oriented either to an examinee H side or to an X-ray source 11a side.

In this embodiment, the heel effect compensation filter 14 is formed as a single sheet. However, the filter may be formed of a plurality of separate sheets, as long as a distance in the filter through which the X-ray flux transmits is equal to the thickness distribution of the filter 14.

Figure 3B:
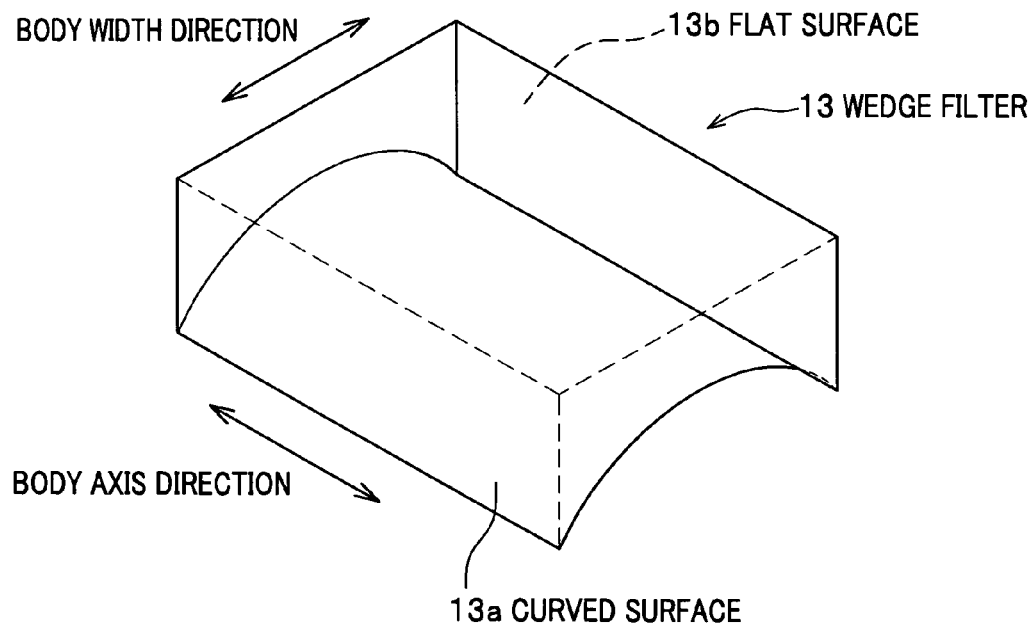

As shown in FIG. 3(b), in the wedge filter 13, the examinee H-side transmissive surface is configured as a cylindrical concave surface extending in the body axis direction and an X-ray source 11a side transmissive surface is configured as a flat surface 13b. The wedge filter 13 has a function of adjusting the intensity of the X-ray flux XR around a torso of the examinee H, and is disposed between the X-ray source 11a and the collimator 12 at a position proximate to the collimator 12.

It should be noted that the wedge filter 13 may be disposed between the collimator 12 and the examinee H, or between the collimator 12 and the heel effect compensation filter 14.

(Usage)

Usage of the X-ray CT scanner 1 of the present invention will be described in reference to FIG. 1.

First, an examinee H is laid on the horizontal platform B positioned below the X-ray source 11a of the X-ray irradiator 10. When the X-ray flux XR is irradiated from the X-ray source 11a under this condition, the X-ray flux XR transmits through the wedge filter 13 while adjusted so that the X-ray intensity angular distribution becomes uniform in the body width direction, then reaches the collimator 12. The X-ray flux XR that has been limited the irradiation area thereof by the opening 12a of the collimator 12 transmits through the heel effect compensation filter 14, while the X-ray intensity angular distribution is adjusted to become uniform in the body axis direction, then reaches the examinee H. The X-ray flux XR that has transmitted through the examinee H reaches a large number of the detection means 20, while the X-ray intensity angular distribution in the body axis direction is kept uniform.

Since the heel effect compensation filter 14 has such a configuration, the X-ray intensity angular distribution under the influence of the heel effect of the X-ray flux XR can be made uniform in the body axis direction after the X-ray flux XR transmitted through the heel effect compensation filter 14.

Since the X-ray irradiator 10 has such a configuration, the examinee H is prevented from being unnecessarily exposed.

In addition, since the X-ray CT scanner 1 has such a configuration, the X-ray intensity angular distribution of the X-ray flux XR can be made uniform at a predetermined distance FCD from the X-ray source 11a, and the examinee H is prevented from being unnecessarily exposed.

Second Embodiment

Figure 8A:
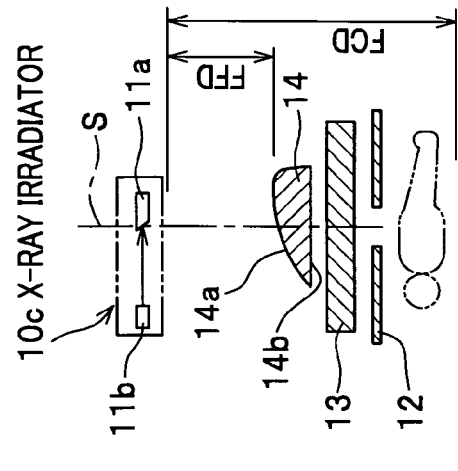
FIG. 8(a) is a diagram showing one example of an X-ray irradiator according to a second embodiment of the present invention, (b) is a graph of an X-ray intensity angular distribution according to the second embodiment, (c) is a diagram showing one example of an X-ray irradiator according to a third embodiment of the present invention, (d) is a graph of an X-ray intensity angular distribution according to the third embodiment, (e) is a diagram showing one example of an X-ray irradiator according to a fourth embodiment of the present invention, and (f) is a graph of an X-ray intensity angular distribution according to the fourth embodiment.

An X-ray CT scanner according to a second embodiment of the present invention is different from the first embodiment in that, with respect to the X-ray irradiator 10a, a flat surface 14b of the heel effect compensation filter 14 as an X-ray flux XR-incoming side transmissive surface is formed on an X-ray source 11a side, and that a cylindrical convex surface 14a as an X-ray flux XR-outgoing side transmissive surface is formed on an examinee H-side, as shown in FIG. 8(a).

When a flat surface 14b of the heel effect compensation filter 14 is disposed between the collimator 12 and the examinee H at a position proximate to the collimator 12 and at a predetermined distance FFD away from the X-ray source 11a, the X-ray intensity angular distribution of the X-ray flux XR becomes uniform at a predetermined distance FCD away from the X-ray source 11a, continuously along a body axis direction in the X-ray flux irradiated space V.

Figure 8B:
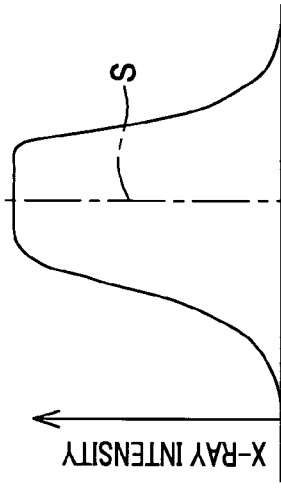

Even when the heel effect compensation filter 14 is placed as explained above, like the first embodiment, as shown in FIG. 8(b), at a predetermined distance FCD from the X-ray source 11a (by the detection means 20), the X-ray intensity angular distribution of the X-ray flux XR can be made uniform, and the examinee H is prevented from being unnecessarily exposed.

Third Embodiment

Figure 8C:
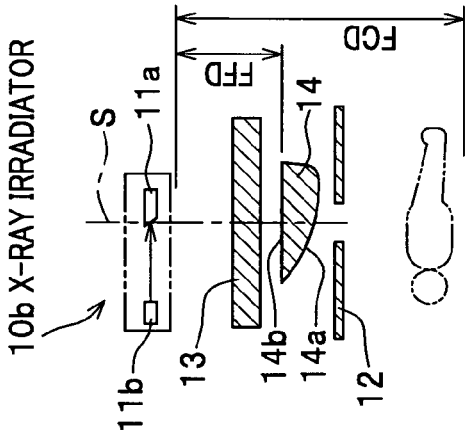

An X-ray CT scanner according to a third embodiment of the present invention is different from the first embodiment in that, with respect to the X-ray irradiator 10b, a flat surface 14b of the heel effect compensation filter 14 as an X-ray flux XR-incoming side transmissive surface is formed on an X-ray source 11a side, and that a cylindrical convex surface 14a as an X-ray flux XR-outgoing side transmissive surface is formed on an examinee H-side, and that the heel effect compensation filter 14 is disposed between the wedge filter 13 positioned on an X-ray source 11a side and the collimator 12, as shown in FIG. 8(c).

Figure 8D:
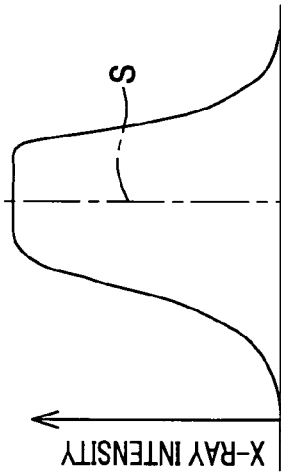

Even when the heel effect compensation filter 14 is placed as explained above, like the first embodiment, as shown in FIG. 8(d), at a predetermined distance FCD from the X-ray source 11a (by the detection means 20), the X-ray intensity angular distribution of the X-ray flux XR can be made uniform, and the examinee H is prevented from being unnecessarily exposed.

Fourth Embodiment

Figure 8E:
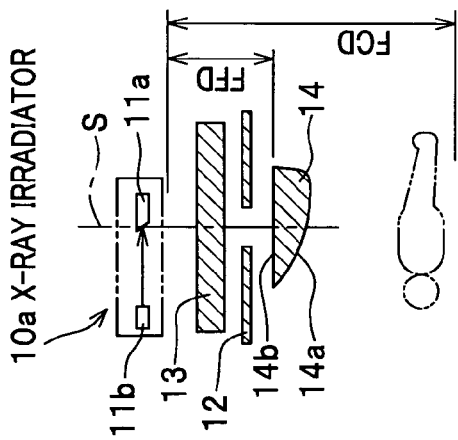

An X-ray CT scanner according to a fourth embodiment of the present invention is different from the first embodiment in that, with respect to the X-ray irradiator 10c, a cylindrical convex surface 14a of the heel effect compensation filter 14 as an X-ray flux XR-incoming side transmissive surface is formed on an X-ray source 11a side, that a flat surface 14b as an X-ray flux XR-outgoing side transmissive surface is formed on an examinee H side, and that the heel effect compensation filter 14 is disposed between the wedge filter 13 positioned on an X-ray source 11a side and the X-ray source 11a, as shown in FIG. 8(e).

Figure 8F:
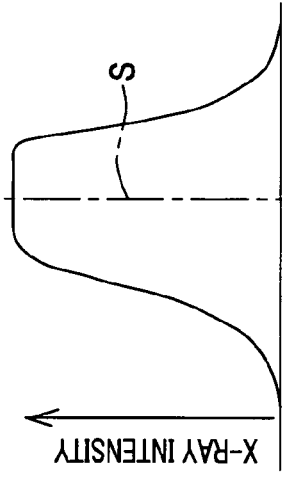

Even when the heel effect compensation filter 14 is placed as explained above, like the first embodiment, as shown in FIG. 8(f), at a predetermined distance FCD from the X-ray source 11a (by the detection means 20), the X-ray intensity angular distribution of the X-ray flux XR can be made uniform, and the examinee H is prevented from being unnecessarily exposed.

Fifth Embodiment

Figure 9:
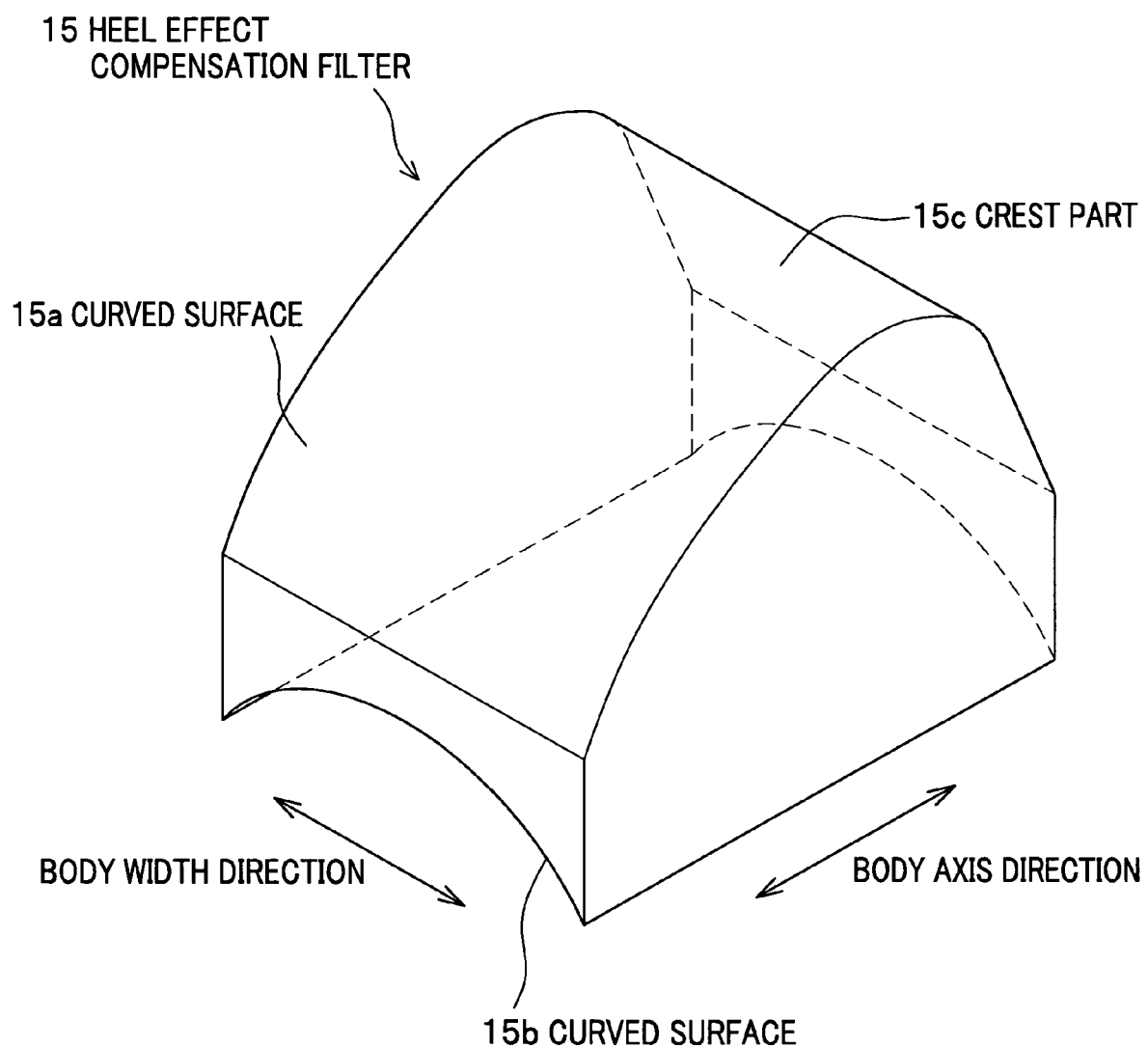
FIG. 9 is a perspective view showing one example of a heel effect compensation filter to be used in an X-ray irradiator according to a fifth embodiment of the present invention.

An X-ray CT scanner according to a fifth embodiment of the present invention is different from the first embodiment in that, with respect to the X-ray irradiator, a heel effect compensation filter 15 shown in FIG. 9 has a cylindrical convex surface 15a with a curve being formed in the body axis direction of the examinee H and a cylindrical concave surface 15b with a curve being formed in the body width direction on the opposite side to the cylindrical convex surface 15a.

The heel effect compensation filter 15 has a cylindrical convex surface 15a with a curve being formed in the body axis direction of the examinee H and a cylindrical concave surface 15b with a curve being formed in the body width direction on the opposite side to the cylindrical convex surface 15a. On the cylindrical convex surface 15a, a crest part 15c is formed at a position away from the irradiation axis S of the X-ray flux XR.

In other words, the heel effect compensation filter 15 has a shape obtained by adjoining the flat surface 14b of the heel effect compensation filter 14 used in the first embodiment to the flat surface 13b of the wedge filter 13 of the first embodiment. Preferably, the heel effect compensation filter 14 and the wedge filter 13 used in the first embodiment are integrally formed.

When the X-ray flux XR transmits through the heel effect compensation filter 15, at a predetermined distance FCD from the X-ray source 11a (the detection means 20), the X-ray intensity angular distribution of the X-ray flux XR can be made uniform along the body axis direction of the examinee H perpendicular to the irradiation axis S of the X-ray flux XR. In addition, the intensity of the X-ray flux XR can be adjusted in the body width direction of the examinee H in accordance with a difference in a thickness of the examinee H. Therefore, while preventing the examinee H from being unnecessarily exposed, clear slice data can be obtained.

As shown above, according to the heel effect compensation filters 14 and 15 of the present invention, when irradiating the X-ray flux XR on the subject H, a nonuniform X-ray intensity angular distribution due to the heel effect of the X-ray flux XR can be adjusted to become uniform in the body axis direction.

Further, the prevent inventors made intensive and extensive studies from detailed technical viewpoints with respect to the heel effect compensation filters 14 and 15 of the present invention. As a result, novel functions, effects and applications were found which had not been speculated from the conventional knowledge of heel effect.

Herein, the novel functions, effects and applications of the heel effect compensation filters 14 and 15 of the present invention will be described.

The X-ray flux XR irradiated from the X-ray source 11a of the X-ray CT scanner 1 is typically a continuous X-ray composed of a broad energy spectrum, and for evaluating irradiation quality, effective energy is generally used. The effective energy is an energy value of a monochromatic X-ray that gives a half-value layer equivalent to that of the X-ray flux XR, and can be easily calculated by a conventional method from the half-value layer of the irradiated X-ray flux XR. The half-value layer is represented by a thickness of a filter that halves an amount of outgoing X-ray relative to an amount of incoming X-ray.

The present inventor has studied and found that, in an X-ray irradiator using solely a conventional wedge filter, effective energy of the X-ray flux transmitted through the wedge filter becomes nonuniform in a predetermined direction. Conventionally, in an X-ray irradiator, only dose distribution is taken into account and effective energy distribution has not drawn attention, and disadvantages of nonuniform effective energy of the X-ray flux irradiated on the subject had not even been come to an issue.

As shown in FIG. 1, the X-ray irradiator 10 according to the present embodiment irradiates the X-ray flux XR from the anode (X-ray source) 11a in such a manner that the X-ray intensity angular distribution of the X-ray flux XR transmitted through the examinee H becomes uniform on the platform B-side surface of the detection means 20. The X-ray irradiator 10 includes the cathode 11b, the X-ray source 11a, the collimator 12, the wedge filter 13 having the cylindrical concave surface 13a, and the heel effect compensation filter 14 having the cylindrical convex surface 14a.

In this X-ray irradiator 10, the X-ray flux XR passes through the heel effect compensation filter 14, and therefore the effective energy of the X-ray flux XR in a predetermined direction of the examinee H becomes high and uniform.

The heel effect compensation filter 14 of the present embodiment has a function of adjusting the effective energy of the X-ray flux XR irradiated from the X-ray source 11a to become uniform in a predetermined direction, after the X-ray flux XR transmitted through the heel effect compensation filter 14. Specifically, the heel effect compensation filter 14 is made thicker at positions where the effective energy of the X-ray flux XR that has transmitted through the wedge filter 13 is low, and thinner at positions where the effective energy of the X-ray flux XR that has transmitted through the wedge filter 13 is high. Therefore, on the axial plane containing the beam irradiation axis of the thermoelectron beam flux and the irradiation axis S of the X-ray flux, the effective energy on an axis orthogonal to the irradiation axis S at a predetermined distance from the anode 11a can be made high and uniform.

The reason for obtaining high effective energy is considered that, due to a predetermined thickness distribution of the heel effect compensation filter 14, a low-energy X-ray contained in the X-ray flux XR is absorbed when the X-ray flux XR transmits through the heel effect compensation filter 14, resulting in a shift of energy distribution of the X-ray flux XR to a high-energy side. When the effective energy of the incoming X-ray into the subject H is high, energy absorption becomes poor during the transmission through the subject H, and thus a difference in the effective energy of the outgoing X-ray from the subject becomes small. When such a heel effect compensation filter 14 is employed in the X-ray CT scanner 1 and the like, generation of artifacts, such as a beam hardening artifact, is reduced, and image quality of image data is made uniform and improved in the body axis direction.

Further, as a formula for calculating a thickness distribution of the heel effect compensation filter 14 that makes the effective energy uniform in a predetermined direction, the above-mentioned Formula 1 may be used.

In this embodiment, the heel effect compensation filter 14 is formed as a single sheet. However, the filter may be formed of a plurality of separate sheets, as long as a distance in the filter through which the X-ray flux transmits is equal to the thickness distribution of the filter 14.

In addition, also in a case where the heel effect compensation filter is used for making the effective energy uniform in a predetermined direction, the heel effect compensation filter may be disposed in various ways as shown in the first to fifth embodiments.

It should be noted that the artifact that can be reduced by introducing such a heel effect compensation filter 14 to the X-ray CT scanner 1 and the like is not limited to the beam hardening artifact. For example, a ring-shaped artifact is an artifact of a ring shape generated in image data due to failures of detectors. In general, a computer program is used for detecting and adjusting such a ring-shaped artifact of the image data. However, when a beam hardening artifact is present in the image data together with a ring-shaped artifact, the computer program may not properly detect and adjust the ring-shaped artifact. Therefore, the heel effect compensation filter 14 of the present embodiment can reduce not only a beam hardening artifact in image data, but also other artifacts, such as a ring-shaped artifact.

Referring to FIG. 1, a description will be made below regarding the X-ray CT imaging method which uses a heel effect compensation filter providing a novel function and application in which the effective energy is made high and uniform and artifacts are reduced.

As shown in FIG. 1, an X-ray CT scanner 11 to be used for the X-ray CT imaging method according to the present embodiment includes an X-ray irradiator 10 provided with such a heel effect compensation filter 14, a detection means 20, a platform B and a gantry (not shown). The X-ray flux XR is irradiated on the examinee H lying on the platform B as the X-ray irradiator 10 revolves around the body axis of the subject, while the platform B moves forward and backward. During this movement, the detection means 20 captures the X-ray flux that has transmitted through the examinee and produces slice data, which is then subjected to image processing by a computer (not shown) and converted into image data. Since a structure of the X-ray CT scanner 1 is the same as that described above, the description is omitted.

The X-ray CT imaging method according to the present embodiment is performed in the following manner: first, an examinee H is laid on the horizontal platform B positioned below the X-ray source 11a of the X-ray irradiator 10. When the X-ray flux XR is irradiated from the X-ray source 11a under this condition, the X-ray flux XR transmits through the wedge filter 13, then reaches the collimator 12. The X-ray flux XR that has been limited the irradiation area thereof by the opening 12a of the collimator 12 transmits through the heel effect compensation filter 14, while on the axial plane containing the beam irradiation axis of the thermoelectron beam flux and the irradiation axis of the X-ray flux XR, the effective energy on an axis orthogonal to the irradiation axis at a predetermined distance from the X-ray source 11a is adjusted to become high and uniform, then reaches the examinee H. With such an X-ray flux XR that has transmitted through the heel effect compensation filter 14, energy absorption becomes poor during transmission through the examinee H, and thus a difference in the effective energy of the outgoing X-ray from the subject H becomes small. The X-ray flux XR that has transmitted through the examinee H reaches a large number of the detection means 20, while maintaining the effective energy. The detection means 20 captures the X-ray flux and produces slice data, which is then subjected to image processing by a computer (not shown) to be converted into image data.

According to the X-ray CT imaging method using such a heel effect compensation filter 14, generation of artifacts, especially a beam hardening artifact, can be reduced and quality of image data can be made uniform in the body axis direction and excellent.

The embodiments of the present invention have been described above. However, the present invention is not limited to the embodiments above. For example, the direction of the X-ray flux irradiation may be vertical, horizontal, oblique or the like.

The subject is not limited to a human being, and may be an animal or a plant in general, or structures, such as buildings and machines.

In each embodiment, the wedge filter 13 is present when the X-ray flux XR is irradiated. However, the X-ray flux XR may be irradiated without the wedge filter 13.

In addition, use of the X-ray irradiator 10 of the present invention is not limited to CT, and the X-ray irradiator 10 may be employed in a clinical X-ray device, digital radiography (DR), or other general devices in which the X-ray flux is irradiated.

The angle θ can be appropriately used, even when the width of the opening 12a of the collimator 12 is not evenly placed relative to the irradiation axis S of the X-ray flux XR.

EXAMPLES

The present invention will be explained further in detail below with reference to Examples, though the present invention should not be construed to be limited by the following Examples.

Example 1

A thickness distribution of the heel effect compensation filter 14 used in the first embodiment is calculated from Formula 1.

In the present example, a scanner with a 256-array CT, 120 kv and a wedge for head was used for the X-ray CT scanner 1, and a beam with a width of 138 mm was irradiated in order to obtain a distinct X-ray intensity angular distribution.

The following Formula 6, which is a quadratic expression of a fitting function, was used for fitting.

$$I(\theta) = -10.8 \tan^2\theta + 0.9 \tan\theta + 0.97$$

$$(-6.560 \leq \theta \leq 5.426, \theta: \text{degree})$$

$$I(\theta) = 2124 \tan^2\theta + 3990 \tan\theta + 17.56$$

$$(5.426 \leq \theta \leq 5.899, \theta: \text{degree}) \quad \text{(Formula 6)}$$

Here, Imax and Imin of the X-ray intensity were set to 100% and 74%, respectively.

Under this condition, calculation was made so that the X-ray intensity as a whole becomes 74% when the heel effect compensation filter 14 was used.

Figure 10:
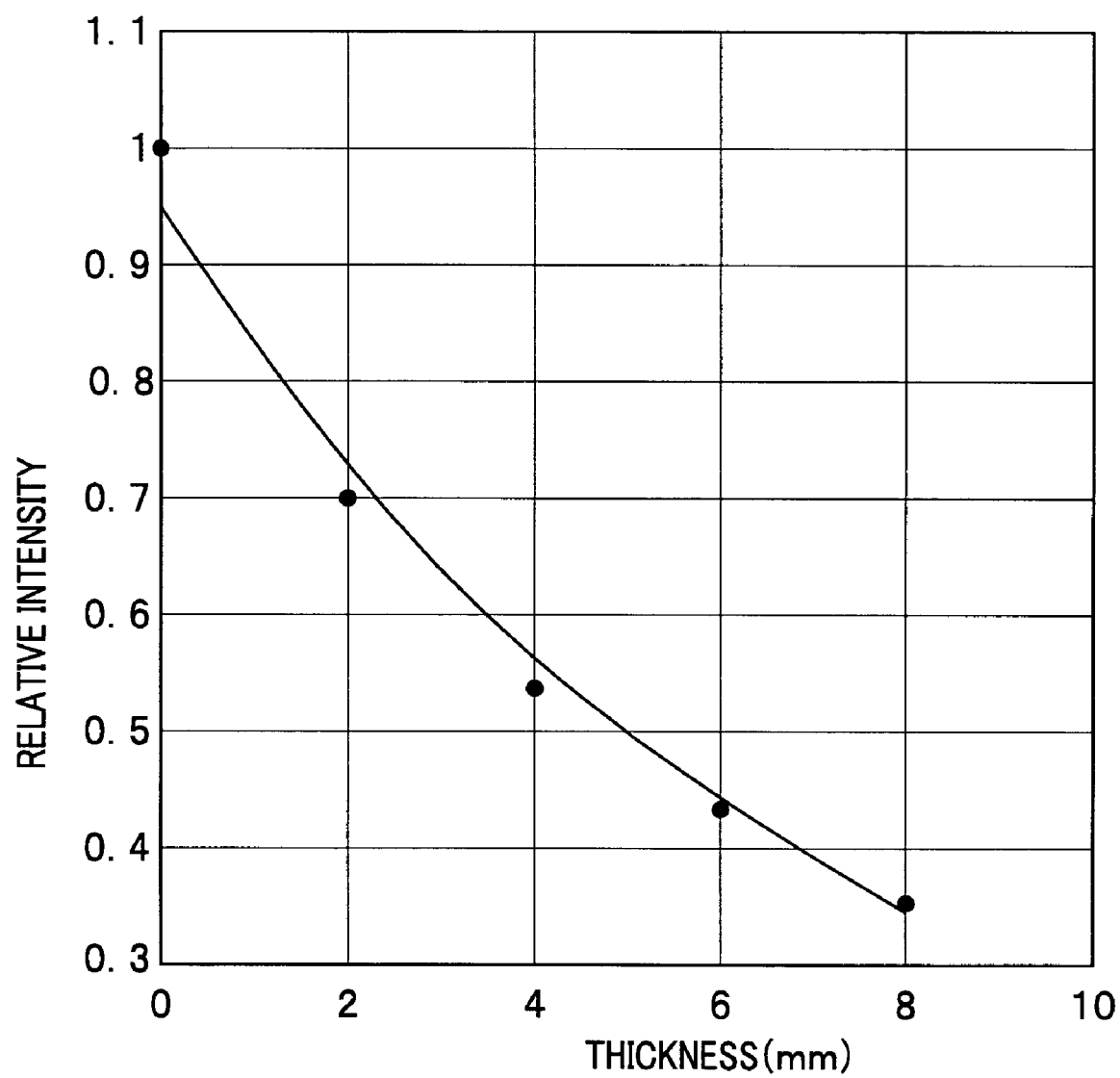
FIG. 10 is a graph showing a relationship between an X-ray intensity and a thickness.

Measurement was also made regarding a thickness and an X-ray transmissivity of the heel effect compensation filter 14, and results are shown in FIG. 10. The relationship is represented by the following Formula 7:

$$I = \text{EXP}(-0.13x) \quad \text{(Formula 7)}$$

where I is an X-ray intensity after transmission and x is a thickness of the heel effect compensation filter 14.

Using this Formula 7, an apparent thickness $L(\theta)$ was calculated which is necessary for making the X-ray intensity to Imin.

$$L(\theta) = 7.67 n(I(\theta)/74) \quad \text{(Formula 8)}$$

With Formula 1, a cone angle was taken into account, and an actual thickness La(O) of the heel effect compensation filter 14 is calculated, where FCD=600 mm and FFD=40 mm.

The resultant thickness $La(\theta)$ of the heel effect compensation filter 14 is shown in FIG. 7.

Example 2

In the present Example, a heel effect compensation filter actually produced was employed in the X-ray CT scanner 1, and effect thereof was demonstrated.

In the present Example, a heel effect compensation filter with a shape which was used in the fifth embodiment was used. Specifically, the heel effect compensation filter has, as shown in FIG. 9, a cylindrical convex surface 15a with a curve being formed in the body axis direction and a cylindrical concave surface 15b with a curve being formed in the body width direction on the opposite side to the cylindrical convex surface 15a. On the cylindrical convex surface 15a, a crest part 15c is formed at a position away from the irradiation axis S of the X-ray flux XR. In other words, the heel effect compensation filter 15 used in the present Example has a shape obtained by adjoining the flat surface 14b of the heel effect compensation filter 14 used in the first embodiment to the flat surface 13b of the wedge filter 13 used in the first embodiment.

For Comparative Example, measurement was made without the heel effect compensation filter but only with the wedge filter 13 used in the first embodiment.

It should be noted that, the heel effect compensation filter 15 used in the present Example and the wedge filter 13 used in Comparative Example are made of the same aluminum material.

Each of the heel effect compensation filters 15 obtained in the present Example and the wedge filter 13 of Comparative Example were installed in the X-ray CT scanner 1 shown in FIG. 1 and were evaluated in the following manner.

[Dose Distribution]

For evaluation of a dose distribution, a 256-array CT was used as an X-ray CT scanner 1. An X-ray was irradiated from a fixed X-ray tube in a vertical downward direction with a tube voltage of 120 kV and a tube current of 200 mA. X-ray intensity was measured with a plurality of detectors set along the body axis direction. For the detector, an Si PIN photodiode dosimeter (S2506-04 by Hamamatsu Photonics K.K) having a detection sensitivity of 2.8 mm (body width direction)×2.8 mm (body axis direction)×2.7 mm (thickness direction) was used.

For each of Example and Comparative Example, the dose distribution in the body axis direction was evaluated.

[Effective Energy]

As described above, the effective energy is an energy value of a monochromatic X-ray that gives a half-value layer equivalent to that of the X-ray flux XR, and can be easily calculated by a conventional method from the half-value layer of the irradiated X-ray flux XR.

The half-value layer is represented by a thickness of a filter that halves an amount of outgoing X-ray relative to an amount of incoming X-ray. Specifically, a fixed X-ray tube was covered with aluminum filters of various thicknesses, an X-ray is irradiated from the X-ray tube in a vertical downward direction, and X-ray intensity was detected with an ionization chamber-type irradiation dosimeter to obtain an irradiation absorption curve. Based on the irradiation absorption curve, the half-value layer was calculated. In the present Example, the ionization chamber-type irradiation dosimeter having a volume of 0.6 ml (C-110 by Applied Engineering Inc.) was used.

For each of Example and Comparative Example, evaluation was made with respect to the effective energy distribution on a plane containing the body axis direction and the body width direction orthogonal to the body axis direction.

[Image Data]

For evaluation of image data, a 256-array CT was used as an X-ray CT scanner 1. Images of the CT phantom placed on the platform B were obtained under the following conditions: a tube voltage of 120 kV, a tube current of 200 mA, an irradiation time of 1 second, a gantry revolution time of 1 second and a slice thickness of 1 mm. For the CT phantom to be used for imaging, a phantom for low contrast evaluation (Calphan 500 by The Phantom Laboratory) was used.

For each of Example and Comparative Example, evaluation was made using image data captured at positions of −40 mm, 0 mm and 40 mm in the body axis direction.

Results of the evaluation will be explained below with reference to the drawings.

Figure 11:
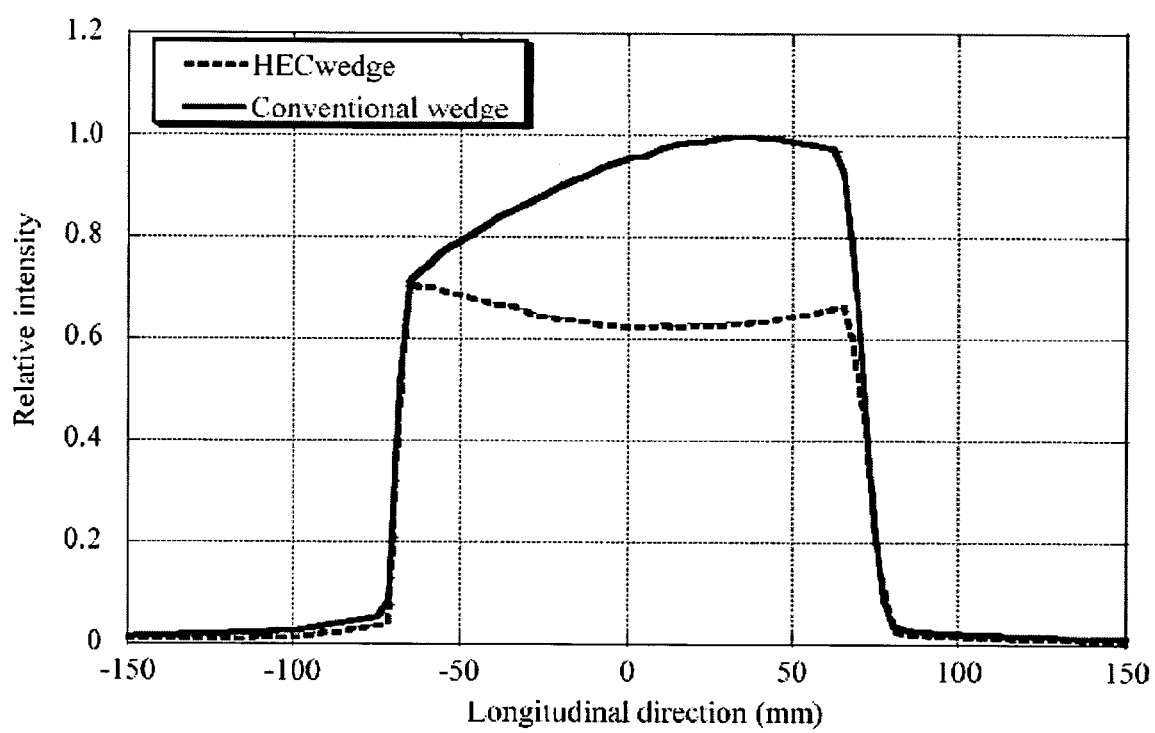
FIG. 11 is a graph showing a result of a dose distribution measurement.

FIG. 11 is a graph showing a result of a dose distribution measurement. In FIG. 11, a vertical axis represents X-ray intensity and a horizontal axis represents a position in the body axis direction (a cathode side is represented by "−" and an anode side is represented by "+", relative to an intersection of the irradiation axis and the body axis). In FIG. 11, a broken line represents a dose distribution in a case where the heel effect compensation filter 15 of the present Example is employed (in the drawing, indicated with "HEC Wedge"), while a solid line represents a dose distribution in a case where solely the wedge filter of Comparative Example is employed (in the drawing, indicated with "Conventional Wedge"). It should be noted that, in FIG. 11, the X-ray intensity on the vertical axis is represented by a relative value in which the maximum X-ray intensity in Comparative Example is taken as 1.0.

As shown in FIG. 11, the present Example shows a low and uniform X-ray intensity distribution along the body axis direction, as compared with Comparative Example having a maximum value.

Moreover, as a result of the low and uniform X-ray intensity distribution in the present Example, an integral dose of the present Example was reduced by 20% as compared with Comparative Example (in FIG. 11, corresponding to area ratio). Therefore, according to the present Example, exposure of the examinee H can be significantly reduced during imaging with the X-ray CT scanner 1.

Though the dose distribution was measured using a dosimeter in the present Example, methods for measuring the dose distribution is not limited to this. For example, in a case where an X-ray tube revolves in the X-ray CT scanner, the X-ray tube can be fixed, the X-ray flux can be irradiated in a vertical downward direction and measured using a predetermined film placed along the body axis direction. A degree of blackness of the film exposed to the X-ray is measured by a densitometer and the like to thereby obtain the dose distribution.

Figure 12A:
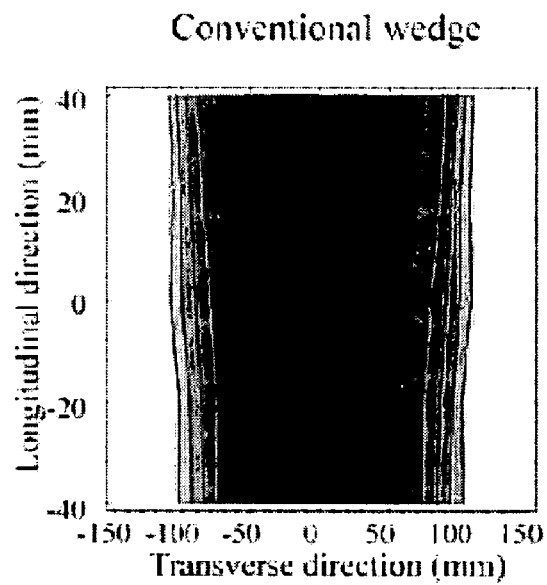
FIG. 12 is a graph showing a result of effective energy measurement. (a) shows a case in which a wedge filter of Comparative Example is used and (b) shows a case in which a heel effect compensation filter of the present invention is used.
Figure 12B:
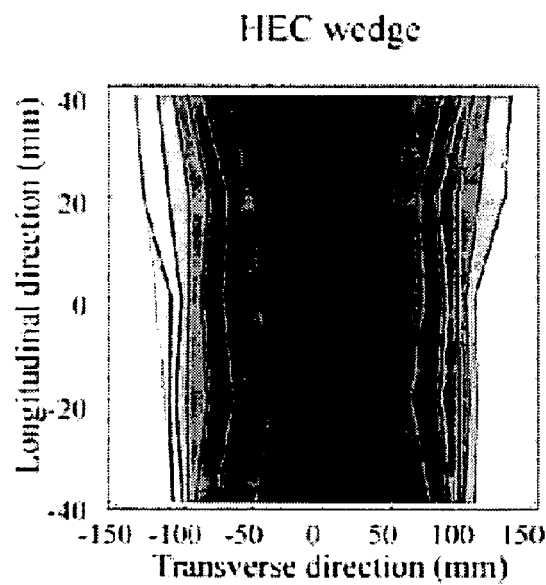

FIG. 12 is a graph showing a result of effective energy measurement. (a) shows a case in which a wedge filter of Comparative Example is used and (b) shows a case in which a heel effect compensation filter of the present Example is used. In FIG. 12, a vertical axis and a horizontal axis are for showing coordinates on the plane containing the body axis direction and the body width direction, where the vertical axis represents a position in the body axis direction (a cathode side is represented by "−" and an anode side is represented by "+", relative to an intersection of the irradiation axis and the body axis), and the horizontal axis represents a position in the body width direction (one side is represented by "−" and the other side as "+", relative to an intersection of the irradiation axis and the body width line). In FIG. 12, coordinates having the same effective energy are connected to one another as an equi-energy line. An area with a deeper color indicates lower effective energy and an area with a lighter color indicates higher effective energy.

As shown in FIG. 12, Comparative Example showed a nonuniform distribution with the cathode side being low and the anode side being high in the body axis direction, while the present Example showed a uniform distribution from the cathode side to the anode side in the body axis direction.

Figure 13:
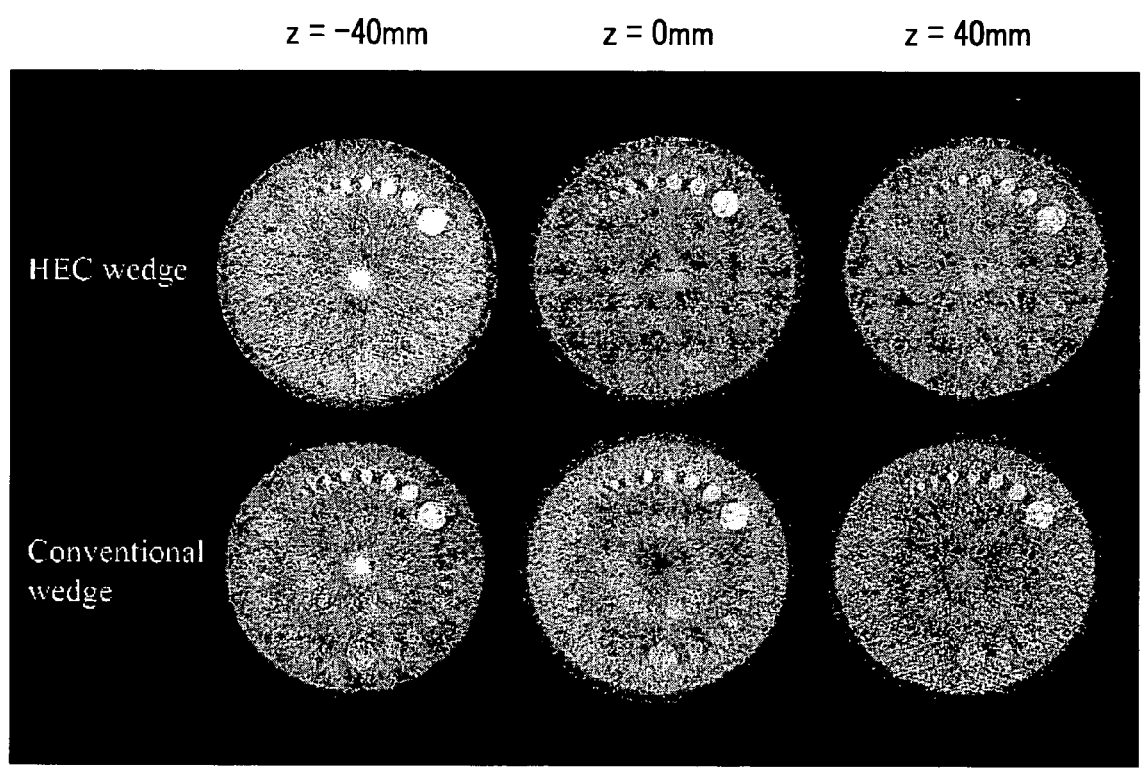
FIG. 13 is image data of a CT phantom, which is imaged.

FIG. 13 is image data of a CT phantom, which is imaged. As shown in FIG. 13, in Comparative Example, a ring-shaped black artifact appears at the center of the phantom as the position approaches the anode side. On the other hand, in the present Example, regardless of the position in the body axis direction, artifacts were not observed and the image quality of the image data was uniform.

In addition, uniformity of image quality of the image data affected by the generation of the artifact can be evaluated using CT value. The CT value can be represented by the following Formula 9.

$$CT \text{ value} = \frac{\mu - \mu_{water}}{\mu_{water}} \times 1000 [HU] \qquad \text{(Formula 9)}$$

In Formula 9, μ represents a ray attenuation coefficient of the subject of interest, $\mu_{water}$ represents a ray attenuation coefficient of water. The CT value of water is defined as 0, of air is defined as −1000. The unit to be used is HU (Hounsfield unit).

When comparison is made between the positions of −40 mm and 40 mm in the body axis direction in Comparative Example, a difference in the CT value of the center part of the image data was 2-3%. On the other hand, when a comparison is made between the positions of −40 mm and 40 mm in the body axis direction in the present Example, a difference in the CT value of the center part of the image data was 0.3%. In short, in the present invention, the difference in the CT value depending on positions in the body axis direction can be reduced as compared with Comparative Example. By reducing the difference in the CT value in this manner, the artifacts can be reduced. Therefore, excellent image data can be obtained in a body part where a low contrast is important factor upon diagnosis, such as a liver, especially in a case where imaging is made with respect to a minute tumor or blood vessel It should be noted that, in the present Example, an effective energy of the X-ray flux was 55 keV. However, this value is merely an example of the effective energy when the artifacts were reduced in the image data, and this should not be construed to limit the present invention.

Though results of the measurement are not shown in the drawing, even when the phantom as an imaging subject is replaced with other kind of phantom, artifacts were observed on the anode side in Comparative Example, while no artifact appeared in image data of the present Example. According to the present invention, regardless of an imaging subject, the artifacts can be reduced and image quality in the body axis direction of the image data can be made uniform.

As shown above, according to the heel effect compensation filter of the present invention, an X-ray CT scanner having 256 arrays of detectors can also reduce the artifacts. In other words, the heel effect compensation filter according to the present invention can be suitably used in an X-ray CT scanner having, for example, 32 arrays or more (such as 32, 40, 64, 124 arrays) of detectors, as a filter which exhibits the following effects: lowering exposure to a subject by making the X-ray angular distribution uniform in a predetermined direction of the X-ray flux irradiated on an examinee; reducing artifacts, especially a beam hardening artifact, by making the effective energy high and uniform in a predetermined direction; and making image quality of image data uniform and improved in the body axis direction.

The invention claimed is:

1. A heel effect compensation filter
which is configured to have a thickness distribution that uniforms an X-ray intensity angular distribution that is nonuniform in a body axis direction of a subject in an X-ray flux irradiated space,
the space being formed by an X-ray flux diverging from an anode in a body width direction of the subject and diverging in a shape of an approximate sector in the body axis direction orthogonal to the body width direction due to the X-ray intensity angular distribution affected by a heel effect, when the X-ray flux generated on the anode by irradiating a thermoelectron beam flux from a cathode to the anode is irradiated on the subject through a wedge filter configured to have a cylindrical concave surface with a curve being formed in the body width direction of the subject, wherein
the thickness distribution is defined by Formula 1:

$$\begin{pmatrix} y' \\ z' \end{pmatrix} = \begin{pmatrix} L(\theta)\cos\theta \\ \frac{FFD}{FCD}(FCD\tan\theta - L(\theta)\sin\theta) \end{pmatrix} \qquad \text{(Formula 1)}$$

$(\theta \leq |\text{cone angle}|)$ where, on a plane containing an irradiation axis of the X-ray flux and a beam irradiation axis of the thermoelectron beam flux, the irradiation axis of the X-ray flux is defined as a Y-axis, and an axis orthogonal to the Y-axis at a distance FCD along the Y-axis in a direction of X-ray flux irradiation is defined as a Z-axis; z' and y' represent positions in corresponding axial directions with the proviso that an intersection point of the Z-axis and the Y-axis is defined as an origin point; FFD is defined as a predetermined distance along the Y-axis from a position of the anode; θ is defined as a predetermined angle within a range of a cone angle symmetrically diverging from the position of the anode relative to the irradiation axis of the X-ray flux; and La(θ) is defined as a length in a y' direction at the angle θ.

2. The heel effect compensation filter according to claim 1, wherein the heel effect compensation filter is separable into pieces and a distance in the heel effect compensation filter through which the X-ray flux transmits during usage is equal to the thickness distribution.

3. The heel effect compensation filter according to claim 1, wherein either of an X-ray flux-incoming side transmissive surface and an X-ray flux-outgoing side transmissive surface is configured as a cylindrical convex surface with a curve being formed in the body axis direction of the subject and the other is configured as a flat surface.

4. The heel effect compensation filter according to claim 1, wherein either of an X-ray flux-incoming side transmissive surface and an X-ray flux-outgoing side transmissive surface is configured as a cylindrical convex surface with a curve being formed in the body axis direction and the other is configured as a cylindrical concave surface with a curve being formed in the body width direction orthogonal to the body axis direction.

5. The heel effect compensation filter according to claim 1, which is employed in an X-ray CT scanner having 32 arrays or more of X-ray detectors.

6. An X-ray irradiator in which a thermoelectron beam flux is irradiated from a cathode to an anode and an X-ray flux generated on the anode is irradiated on a subject, wherein
the heel effect compensation filter according to claim 1 is disposed between the anode and the subject at a predetermined distance,
the filter being configured to adjust the X-ray intensity angular distribution of the X-ray flux to become uniform that is nonuniform in a body axis direction of the subject in an X-ray flux irradiated space,
the space being formed by the X-ray flux diverging from the anode in a body width direction of the subject and diverging in a shape of an approximate sector in the body axis direction orthogonal to the body width direction due to the heel effect.

7. An X-ray CT scanner in which the X-ray irradiator according to claim 6 is employed.

8. A method for X-ray CT imaging which reduces an artifact of image data obtained by an X-ray CT scanner by employing the heel effect compensation filter according to claim 1 in the X-ray CT scanner and reducing a difference in CT value of the image data obtained along a body axis direction.

* * * * *